(12) United States Patent
Vidlund

(10) Patent No.: US 11,439,505 B2
(45) Date of Patent: Sep. 13, 2022

(54) APPARATUS AND METHODS FOR DELIVERY OF PROSTHETIC HEART VALVES

(71) Applicant: Tendyne Holdings, Inc., St. Paul, MN (US)

(72) Inventor: Zachary R. Vidlund, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 274 days.

(21) Appl. No.: 16/935,655

(22) Filed: Jul. 22, 2020

(65) Prior Publication Data

US 2021/0030541 A1 Feb. 4, 2021

Related U.S. Application Data

(60) Provisional application No. 62/882,178, filed on Aug. 2, 2019.

(51) Int. Cl.
| | | |
|---|---|---|
| *A61F 2/24* | (2006.01) | |
| *A61M 25/09* | (2006.01) | |
| *A61M 25/10* | (2013.01) | |
| *A61B 17/34* | (2006.01) | |
| *A61B 17/04* | (2006.01) | |

(52) U.S. Cl.
CPC ........ *A61F 2/2439* (2013.01); *A61B 17/3468* (2013.01); *A61F 2/2418* (2013.01); *A61F 2/2433* (2013.01); *A61M 25/09* (2013.01); *A61M 25/1002* (2013.01); *A61B 2017/0404* (2013.01); *A61F 2220/0008* (2013.01)

(58) Field of Classification Search
CPC .... A61F 2/2439; A61F 2/2418; A61F 2/2433; A61F 2220/0008; A61B 17/3468; A61M 25/09; A61M 25/1002
USPC .................................................. 623/2.1–2.19
See application file for complete search history.

(56) References Cited

U.S. PATENT DOCUMENTS

| | | | |
|---|---|---|---|
| 9,526,487 B2* | 12/2016 | Rahmani ............ | A61B 17/0401 |
| 10,485,652 B2* | 11/2019 | Sengun .............. | A61B 17/0401 |
| 11,284,899 B2* | 3/2022 | Ibrahim ........... | A61B 17/12009 |
| 11,331,186 B2* | 5/2022 | Christianson ......... | A61F 2/2415 |
| 11,337,807 B2* | 5/2022 | Christianson ......... | A61F 2/2436 |
| 2017/0265938 A1* | 9/2017 | Spence ............. | A61B 18/1492 |
| 2020/0030129 A1* | 1/2020 | Earley ................ | A61B 17/0401 |
| 2020/0078164 A1* | 3/2020 | Sengun ................ | A61F 2/0811 |
| 2020/0383717 A1* | 12/2020 | Lederman .......... | A61B 18/1206 |
| 2021/0298898 A1* | 9/2021 | Keidar .................. | A61F 2/2412 |

\* cited by examiner

*Primary Examiner* — Suzette J Gherbi
(74) *Attorney, Agent, or Firm* — Wei & Sleman LLP

(57) ABSTRACT

Apparatus and methods are described herein for use in in establishing an improved AV loop with the use of a pulley/snare device at the base of a ventricle of a heart. In some methods described herein, a pulley/snare device is established to create a path with inherent concentricity to the aortic and mitral valves, allowing the valves to function normally during an interventional procedure in the heart, without impeding the motion of any leaflets. The pulley/snare device described herein minimizes the forces that are applied on the valves or associated cardiac tissue to "make the turn" from the aortic valve to the mitral valve.

20 Claims, 26 Drawing Sheets

APPARATUS AND METHODS FOR DELIVERY OF PROSTHETIC HEART VALVES

CROSS-REFERENCE TO RELATED APPLICATIONS

This application claims the benefit of the filing date of U.S. Provisional Patent Application No. 62/882,178 filed Aug. 2, 2019, the disclosure of which is hereby incorporated herein by reference.

BACKGROUND OF THE INVENTION

Embodiments are described herein that relate to devices and methods for use in the implementation of an improved arteriovenous loop for various different interventional procedures including, for example, the delivery of one or more prosthetic heart valves.

Prosthetic heart valves are used to replace native heart valves that may be damaged or diseased causing heart dysfunction. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary valves. Prosthetic heart valves can be used to replace any of these natural valves. Valvular heart disease, and specifically, aortic, and mitral valve disease is a significant health issue in the United States (US); annually approximately 90,000 valve replacements are conducted in the US.

Procedures for interventions like the placement or repositioning of a prosthetic valve or other treatments of a cardiac dysfunction or dysfunction in the vascular system, often include establishing an arteriovenous loop also called an AV loop. Establishing an AV loop involves delivering a guidewire into the vascular system so that it establishes a continuous path, or loop, for delivery of devices, between an arterial entry point and a venous entry point, and passing through the heart. More specifically, the guidewire may extend between an access point in the femoral vein, through the inferior vena cava, the right atrium, atrial septum, left atrium, mitral valve, left ventricle, aortic valve, aortic arch, abdominal aorta, and an access point in the femoral artery. FIGS. 1A-1C illustrate such an example AV loop using access points in the femoral artery and the femoral vein. An AV loop may be useful to facilitate the advancement and/or deployment of a device used in treatment of the vascular or cardiac condition, such as a prosthetic mitral valve or aortic valve. An AV loop can enable advancement of the device from the venous access, with a significant increase of backup support that provides a stable and rigid rail for the delivery sheath and the device, and two-sided control of the delivery wire.

A traditional AV loop can have associated risks. Among these risks are possible damage to the aortic valve, damage to the mitral valve, acute aortic insufficiency, and acute mitral insufficiency. The root cause of these risks can be identified in the illustration in FIGS. 1B and 1C. After an AV loop is established, for example, using a guide wire or a catheter or the like, the aortic and mitral valve act as a pulley to support linear movement of the guidewire or the catheter, etc. Using the mitral and the aortic valves as a natural pulley can put pressure on these native valves. The pressure and the relative movement of the guidewire or catheter against the aortic and/or mitral valves can have a "cheese cutter" effect and leave permanent damage to the valves. Also, the pinch point created by the AV loop can restrict the aortic and/or mitral valve leaflets, causing acute insufficiency. There is thus a need for an improved method to establish an AV loop during any interventional procedure to treat cardiac or vascular conditions, without damaging the native valves.

BRIEF SUMMARY OF THE INVENTION

Apparatus and methods are described herein for use in in establishing an improved AV loop with the use of a pulley/snare device at the base of a ventricle of a heart. In some methods described herein, a pulley/snare device is established to create a path with inherent concentricity to the aortic and mitral valves, allowing the valves to function normally during an interventional procedure in the heart, without impeding the motion of any leaflets. The pulley/snare device described herein advantageously minimizes the forces applied on the valves or associated cardiac tissue to "make the turn" from the aortic valve to the mitral valve.

DETAILED DESCRIPTION

Figure 1A:
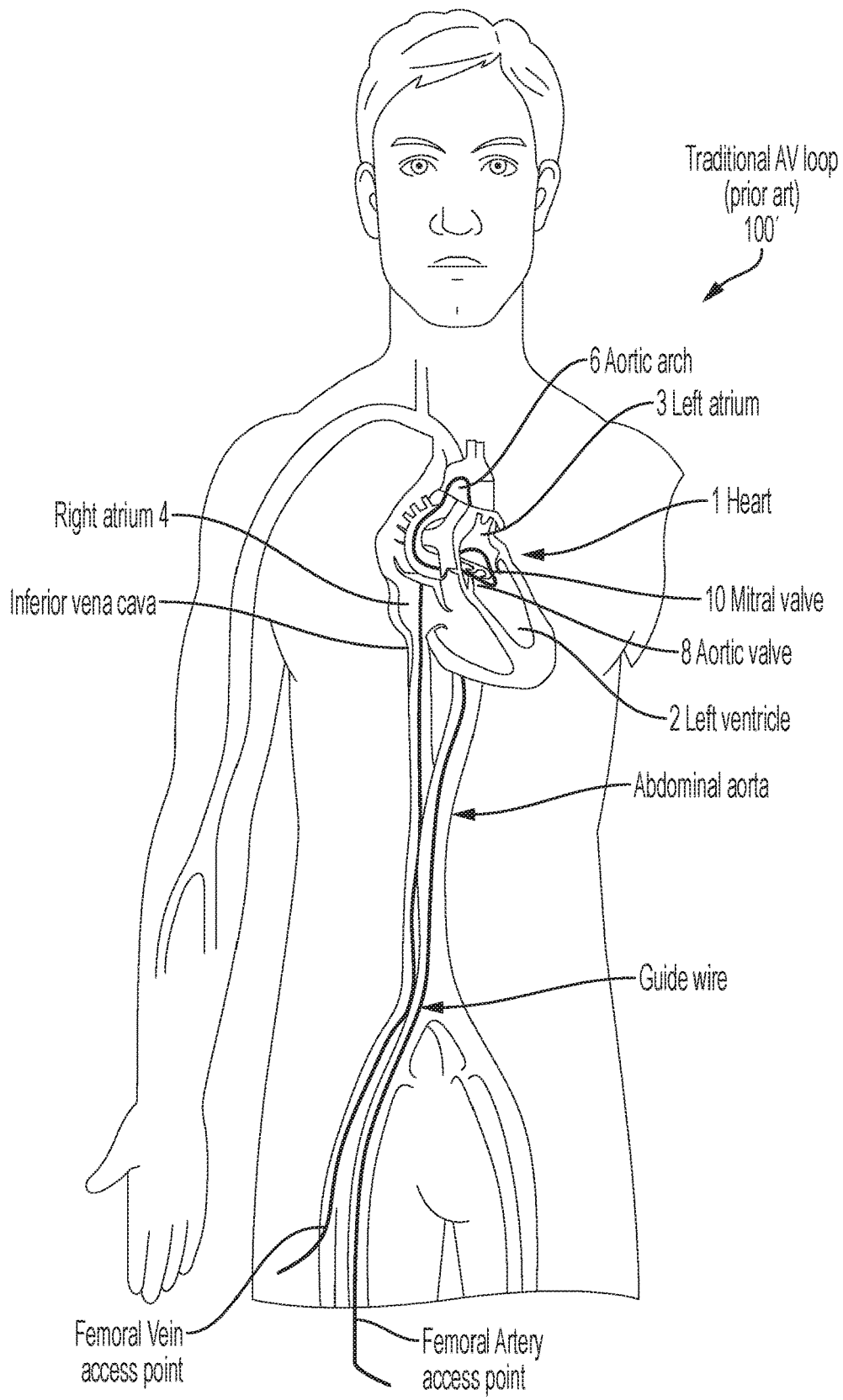
FIG. 1A is a schematic illustration of an example of a traditional arteriovenous (AV) loop in a human heart.
Figure 1B:
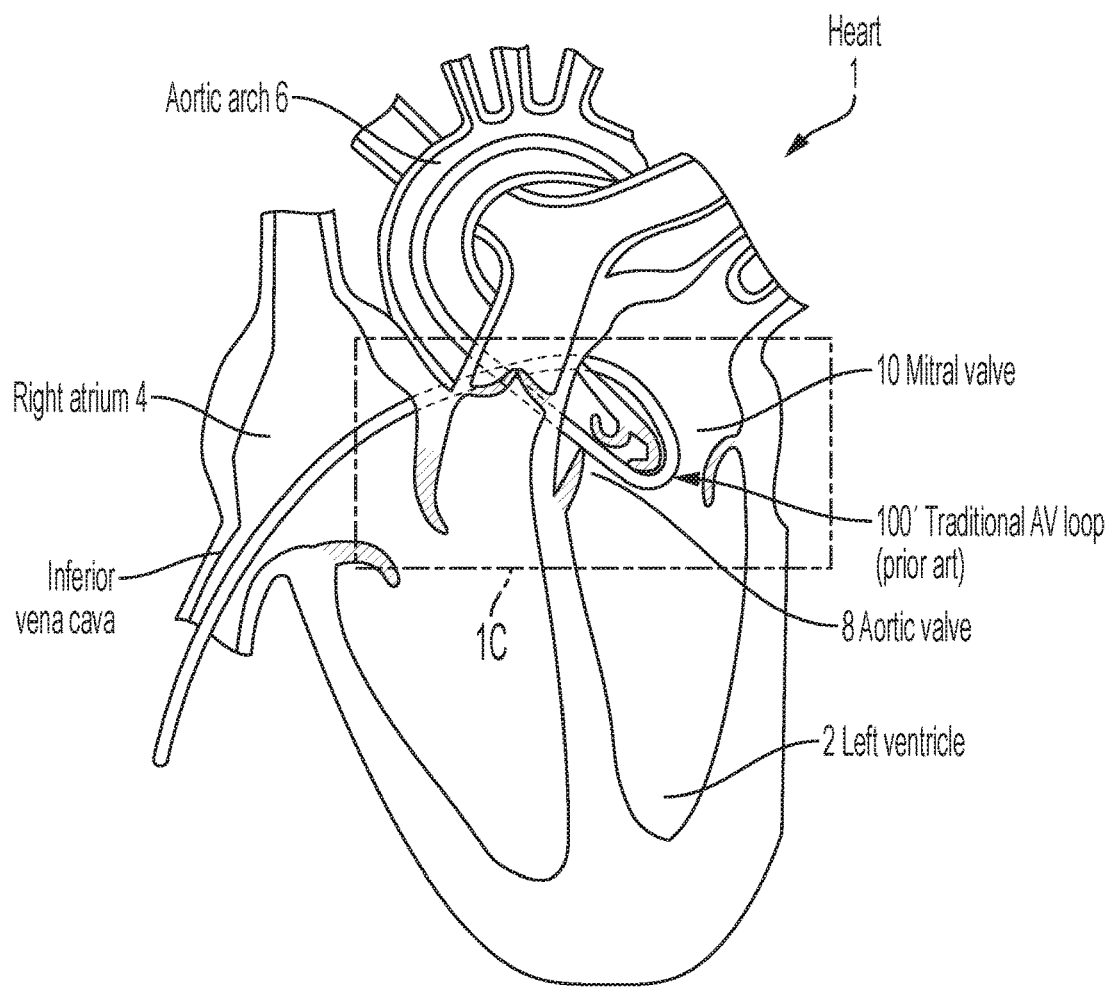
FIG. 1B shows an enlarged view of the heart in FIG. 1A.
Figure 1C:
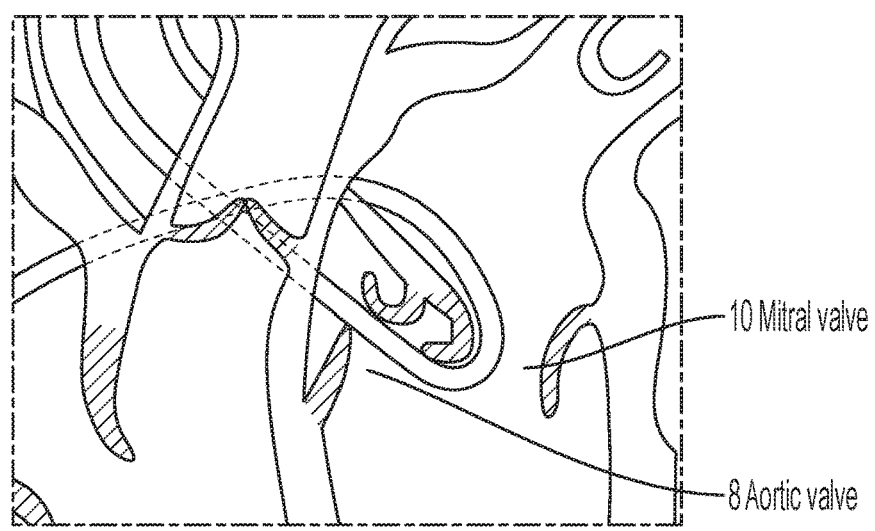
FIG. 1C shows an enlarged view of a portion of the heart in FIG. 1B indicated by the rectangle 1C in FIG. 1B.

Apparatus and methods are described herein for use in establishing an improved AV loop with the use of a pulley/snare device at the base of a ventricle of a heart. As shown in FIGS. 1A and 1B, the current approach to establish a conventional arteriovenous (AV) loop 100' involves drawing a guidewire against, and across, native cardiac tissue, such as the tissue associated with the native mitral valve and/or the native aortic valve. However, the forces exerted on the cardiac tissue supporting the conventional AV loop during establishment and use of the AV loop can be detrimental to the functioning of the aortic and the mitral valves and to cardiac health. According to the methods disclosed herein, the pulley/snare device established at the base of a ventricle of the heart creates a path with inherent concentricity to the aortic and mitral valve, allowing the valves to function normally without impeding the motion of any leaflets, as well as removing any force applied on the valves or associated cardiac tissue to "make the turn" from aortic to mitral valve.

Figure 2:
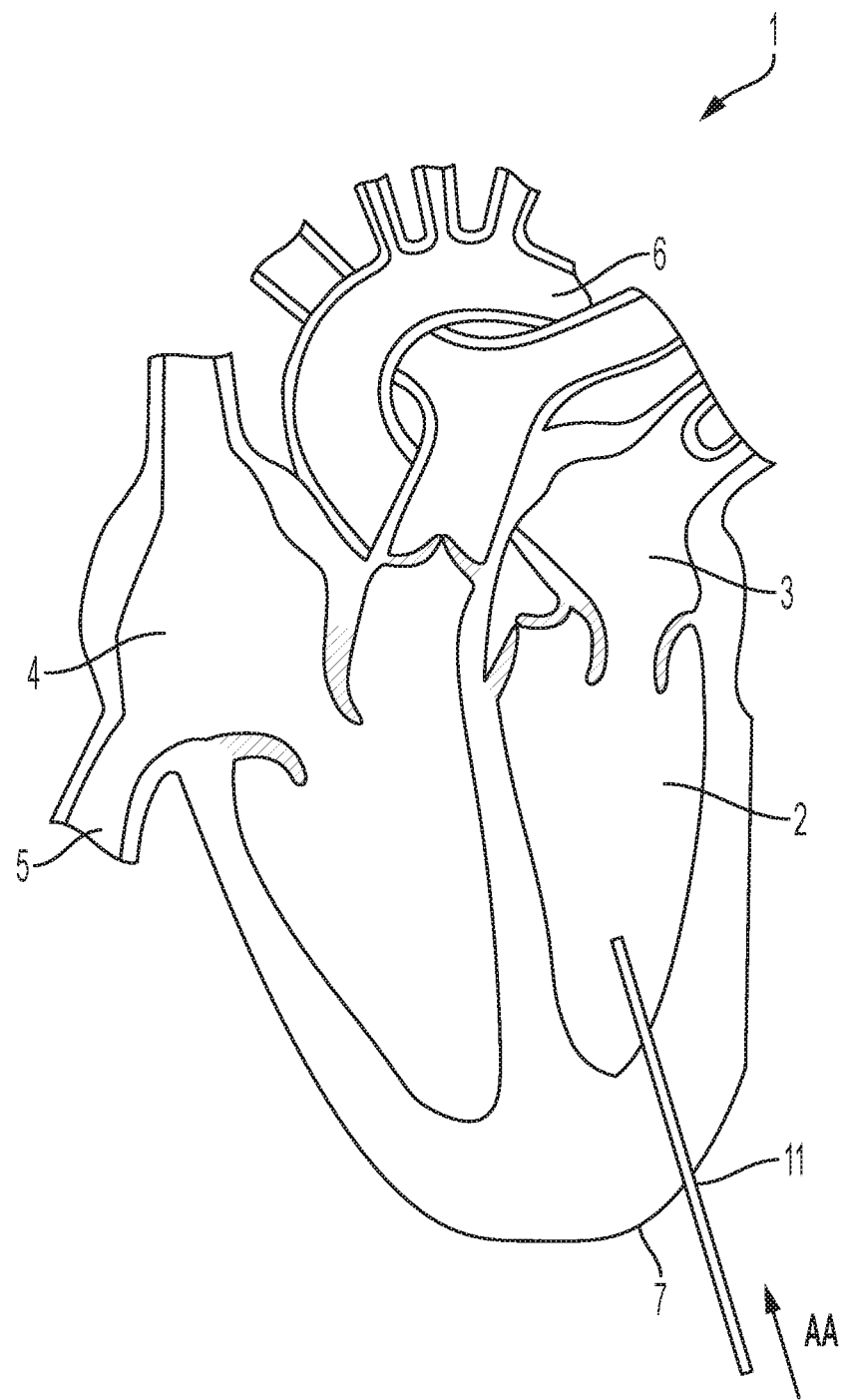
FIG. 2 is a schematic illustration of the insertion of a needle at the apex of a heart, during an interventional heart procedure, according to an embodiment.
Figure 3:
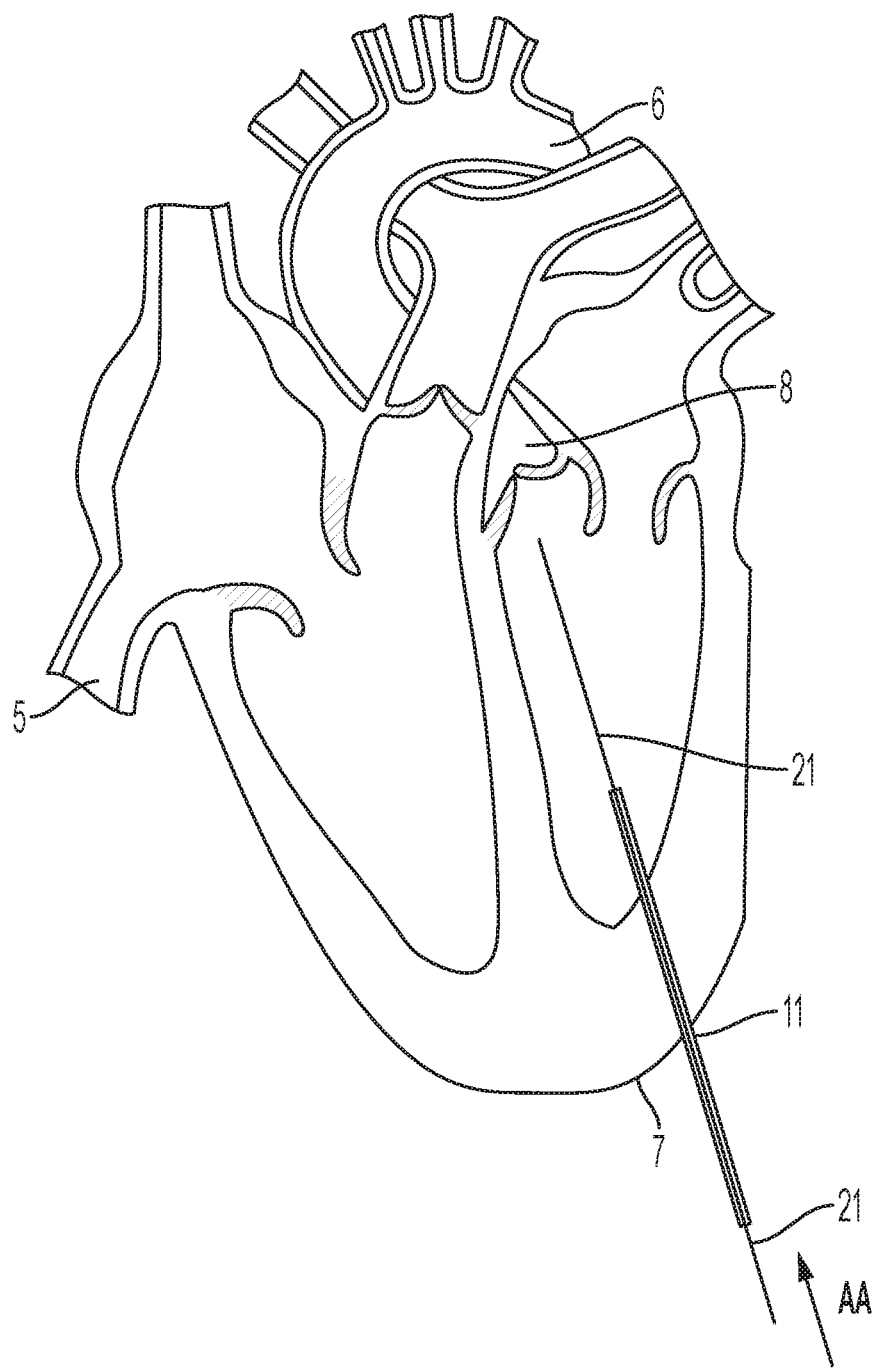
FIG. 3 is a schematic illustration of a first guidewire inserted through the needle of FIG. 2, during the interventional heart procedure.

FIGS. 2-13 illustrate a procedure to establish an improved AV loop with a pulley device positioned within the left ventricle of a heart 1. As shown in FIG. 2, a first needle 11 is inserted into the left ventricle 2 of the heart 1 via the apex 7 of the heart, in the direction indicated by the arrow AA. The apex 7 of the heart 1 may be accessed for insertion of the first needle 11 by any appropriate technique, for example percutaneously through an access sheath delivered by a Seldinger technique, or by direct access via an incision such as a mini thoracotomy. As shown in FIG. 3, a distal end of a first guidewire 21 is introduced into the left ventricle 2 of the heart 1 via a lumen of the first needle 11, in the direction indicated by the arrow AA. The first needle 11 may then be withdrawn proximally from the apex 7 of the heart, over the first guidewire.

Figure 4:
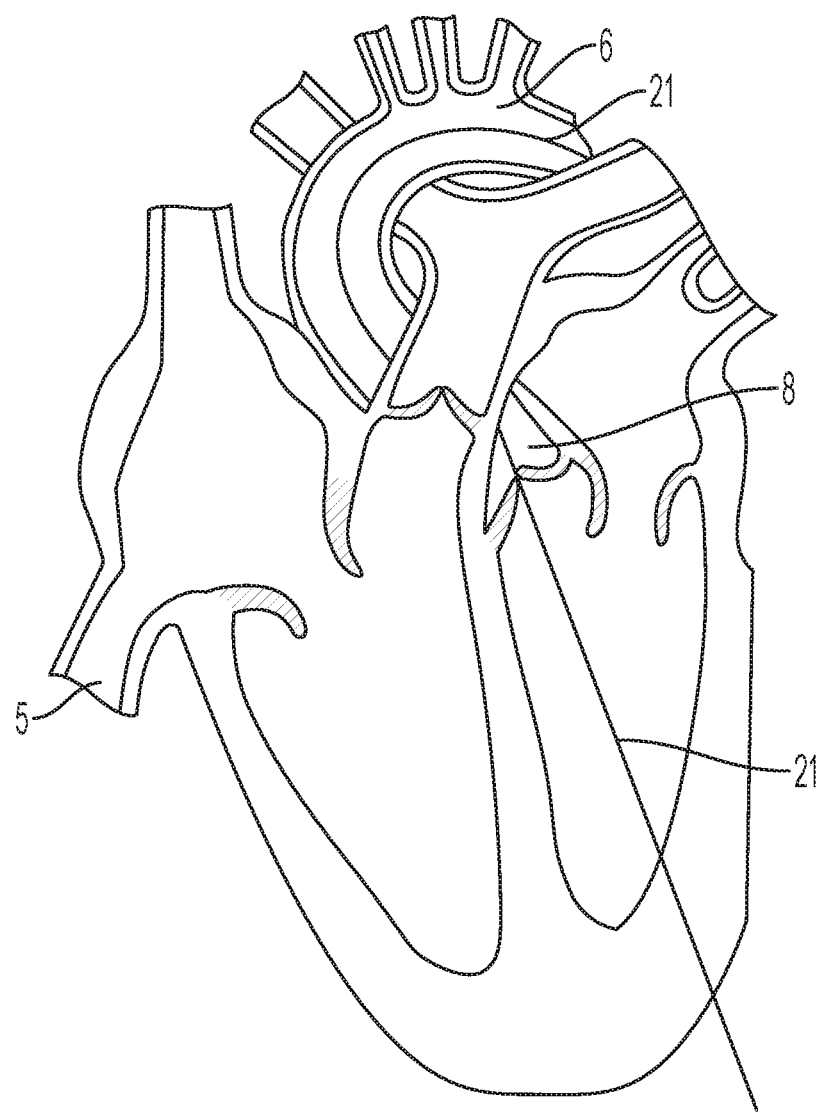
FIG. 4 is a schematic illustration of the guidewire of FIG. 3 advanced through an aortic arch of the heart towards a femoral artery.

The distal end of first guidewire 21 is then routed through the aortic valve 8 and the aortic arch 6, as shown in FIG. 4, and can then be routed through the abdominal aorta to a femoral artery 12. The distal end of the first guidewire 21 may be exteriorized from the femoral artery 12 at an access point in a leg of the subject, e.g. at a first access point 9, as shown in the schematic illustration of a portion of the femoral artery 12 of FIG. 5. The first access point 9 may be established using, for example, a conventional Seldinger technique to insert an access sheath into the femoral artery. The distal end of the first guidewire 21 may be snared using a first snare device 31 introduced into the femoral artery via the access sheath at the access point 9 in the leg, and exteriorized.

Figure 5:
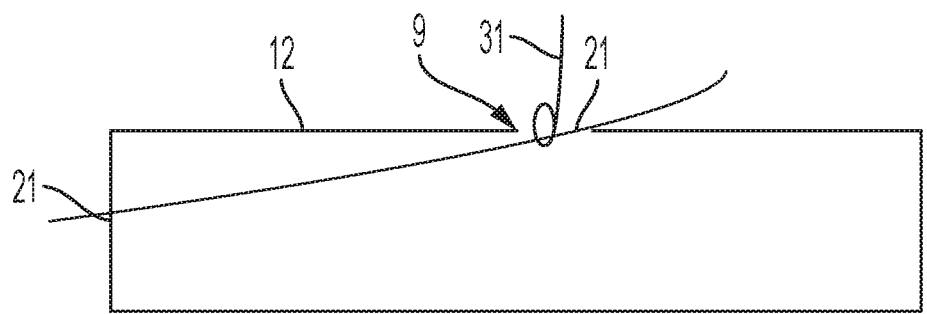
FIG. 5 is a schematic illustration of a portion of a femoral artery in a leg showing the first guidewire of FIG. 3 advanced through the femoral artery and snared by a first snare device.
Figure 6:
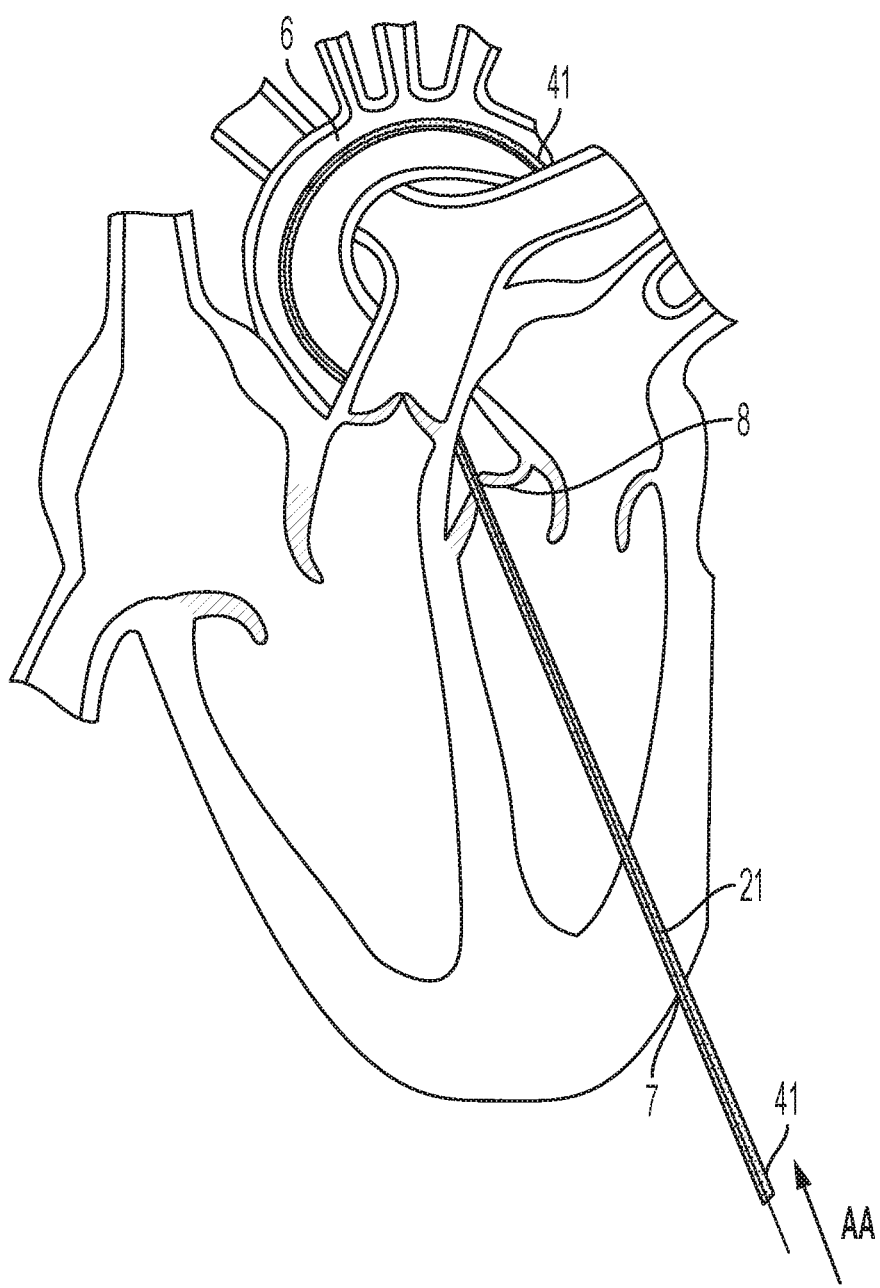
FIG. 6 is a schematic illustration of a microcatheter routed over the first guidewire shown in FIG. 4 from the apex to the femoral artery.

After exteriorization of the distal end of the first guidewire 21, as shown in FIG. 5, a microcatheter 41 may be disposed over the first guidewire 21 and delivered into the left ventricle 2 through the opening in the apex 7 of the heart. The distal end of the microcatheter 41 may then be advanced in the direction indicated by the arrow AA and routed over the first guidewire 21, as shown in FIG. 6, through the aortic valve 8 and the aortic arch 6 of the heart, through the abdominal aorta and femoral artery 12 and exteriorized at the first access point 9. The first guidewire 21 may then be withdrawn from the body through the microcatheter 41. The microcatheter 41 can be any suitable microcatheter, preferably about 3-4 Fr in size, that can accommodate a snare, such as a second snare device 32, within its lumen. Suitable microcatheters and snares are often provided together as a kit.

Figure 7:
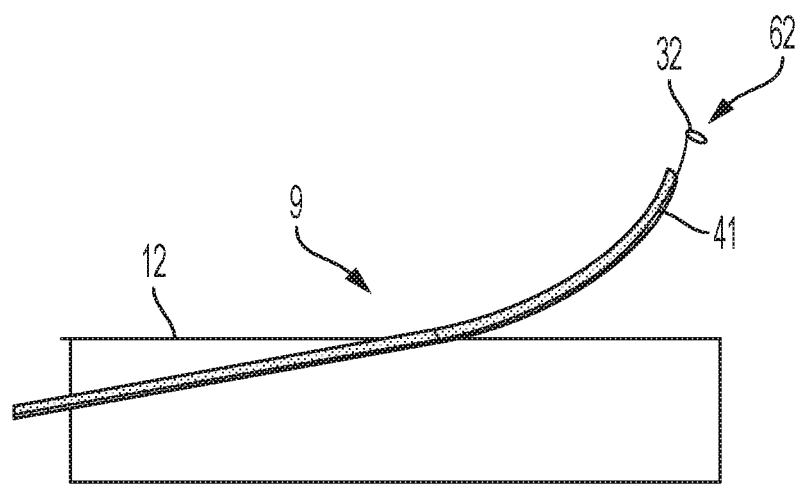
FIG. 7 is a schematic illustration of a portion of a femoral artery in a leg showing a distal end of the microcatheter in FIG. 6, extending outside of the leg and a second snare device disposed through the microcatheter.

Second snare device 32 has a loop end 62 and an opposite, wire end. The wire end can be introduced into the lumen of the microcatheter 41 at the first access point 9, and delivered retrograde through the vasculature, aortic valve 8, and ultimately exteriorized at the apex 7 of the heart. As shown in FIG. 7, this leaves the loop end 62 of second snare device 32 near the distal end of the microcatheter 41.

Figure 8:
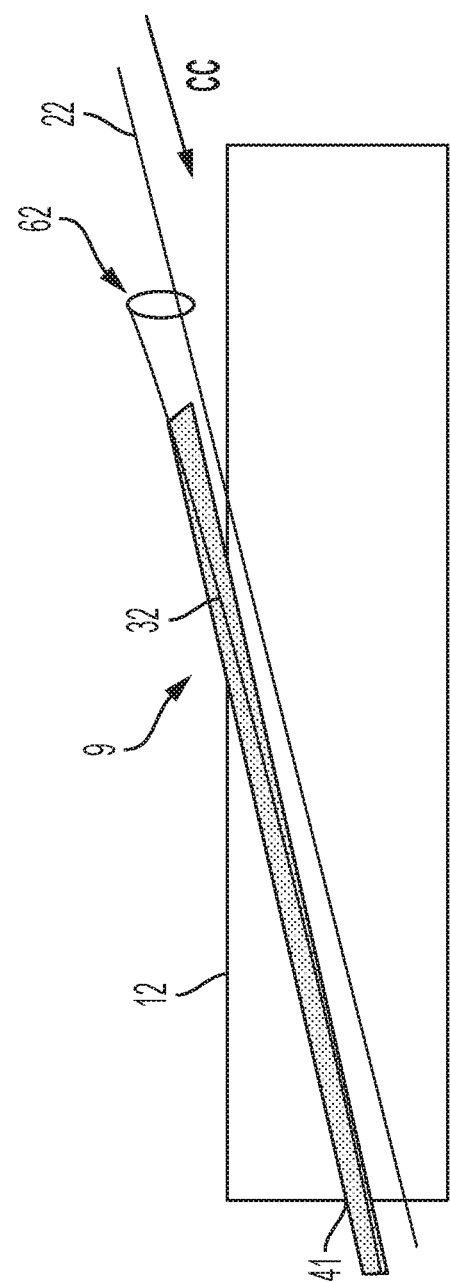
FIG. 8 is a schematic illustration of the femoral artery in a leg and distal end portion of the microcatheter of FIGS. 6 and 7 with the first guidewire removed, and showing a loop end of the second snare device snaring a second guide wire routed alongside the microcatheter.
Figure 9:
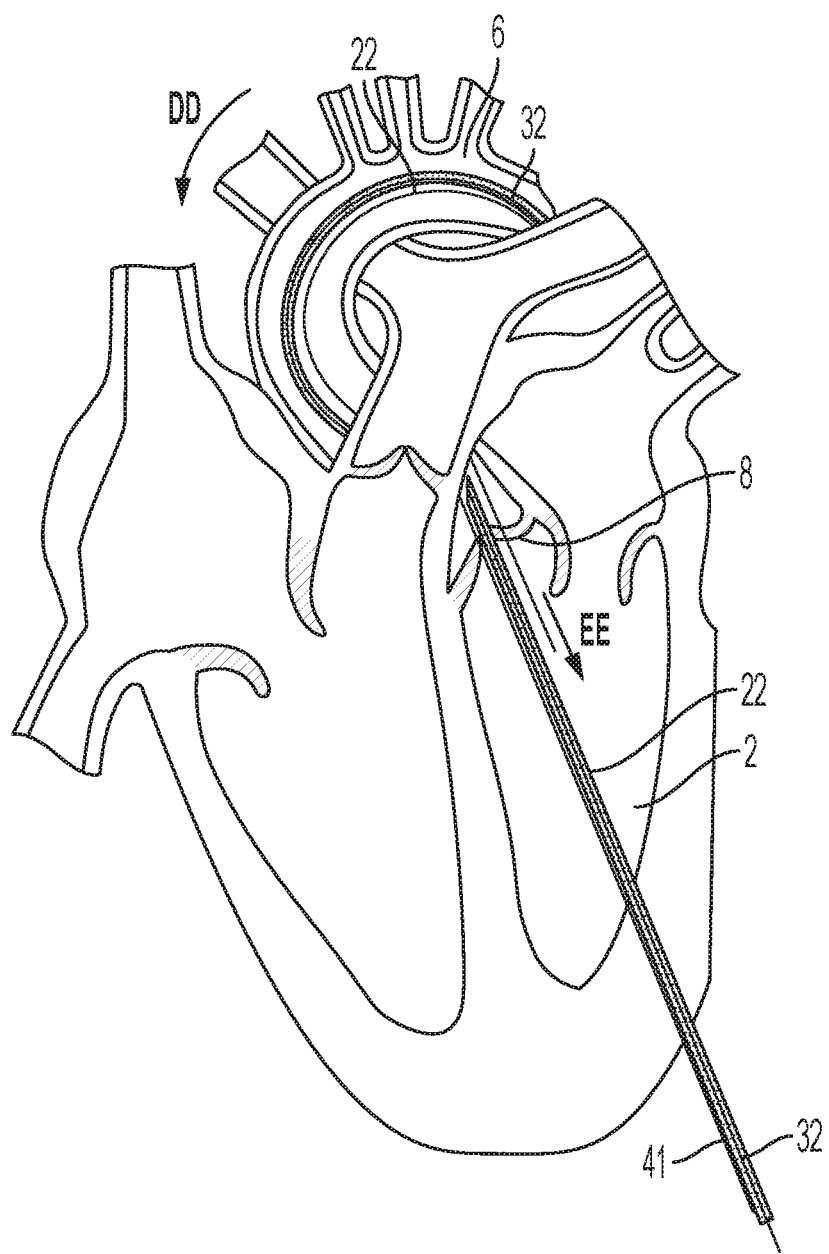
FIG. 9 is a schematic illustration of the heart showing the microcatheter with a loop end of the second snare device disposed outside the apex of the heart and the second guide wire passed through the second snare device and routed alongside the microcatheter with a free end in a left ventricle of the heart.

A distal end of a second guidewire 22 may then be inserted through the loop end 62 of the second snare device 32 and then advanced into the femoral artery 12, alongside the microcatheter 41, as shown in the schematic illustration of a portion of the femoral artery 12 of FIG. 8. The second guidewire 22 is then advanced within the femoral artery 12 in the direction indicated by the arrow CC in FIG. 8. As shown in FIG. 9, the second guidewire 22 is ultimately routed retrograde alongside the microcatheter 41 through the aortic arch 6, the aortic valve 8, and into the left ventricle 2 of the heart, advancing into the left ventricle in the direction indicated by the arrow EE. The distal end of the second guidewire 22 is temporarily positioned within the left ventricle 2.

Figure 10A:
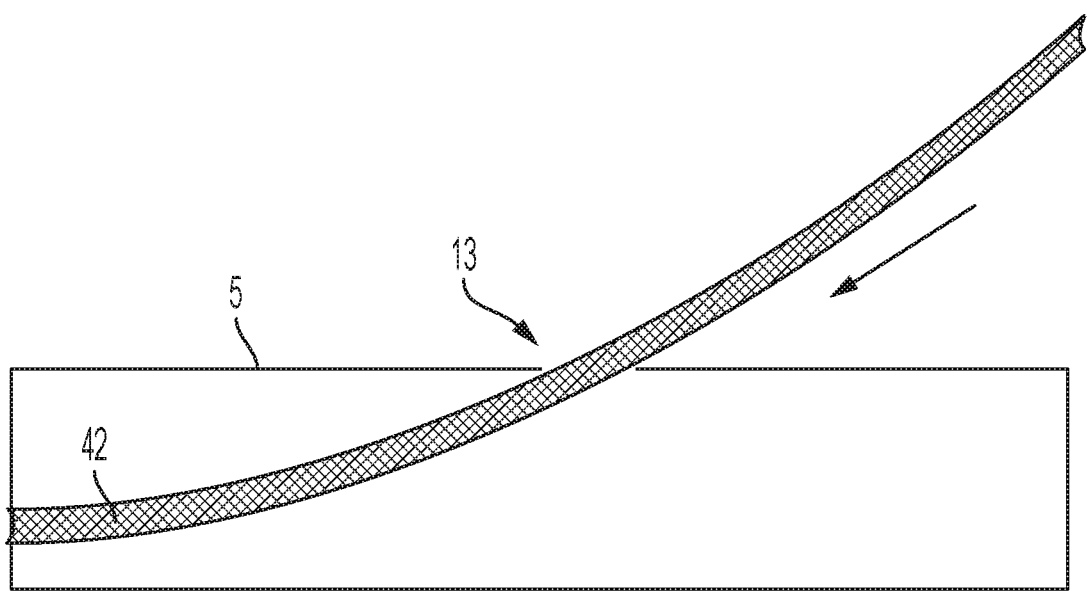
FIG. 10A is a schematic illustration of a portion of a femoral vein in a leg showing a distal end of a steerable catheter being advanced into the femoral vein.
Figure 10B:
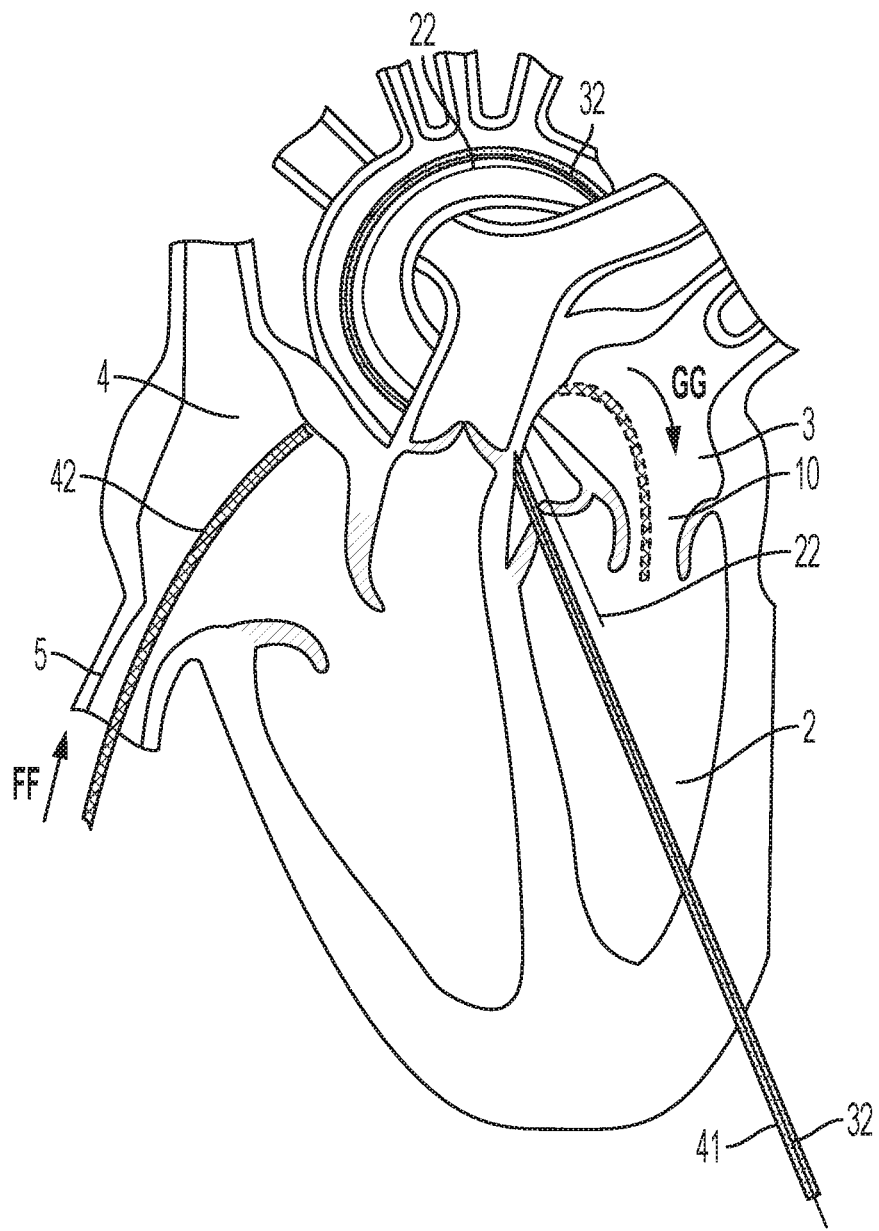
FIG. 10B is a schematic illustration of the heart showing the steerable catheter having been introduced via the femoral vein and a transeptal puncture in the heart, and routed towards the second guidewire with the free end disposed within the left ventricle.

A femoral vein 5 of the subject may be accessed in the same manner as the femoral artery 12, e.g. by a Seldinger technique, to establish a second access point 13 in the leg of the subject, as shown in FIG. 10A. A steerable catheter 42 is introduced into the second access point 13, and routed in conventional fashion into the right atrium 4 of the heart 1. The steerable catheter 42 is then introduced into the left atrium 3 of the heart via a transeptal puncture, as illustrated in FIG. 10B, and advanced in the direction indicated by the arrow GG, through the mitral valve 10, and into the left ventricle 2 of the heart.

Figure 11:
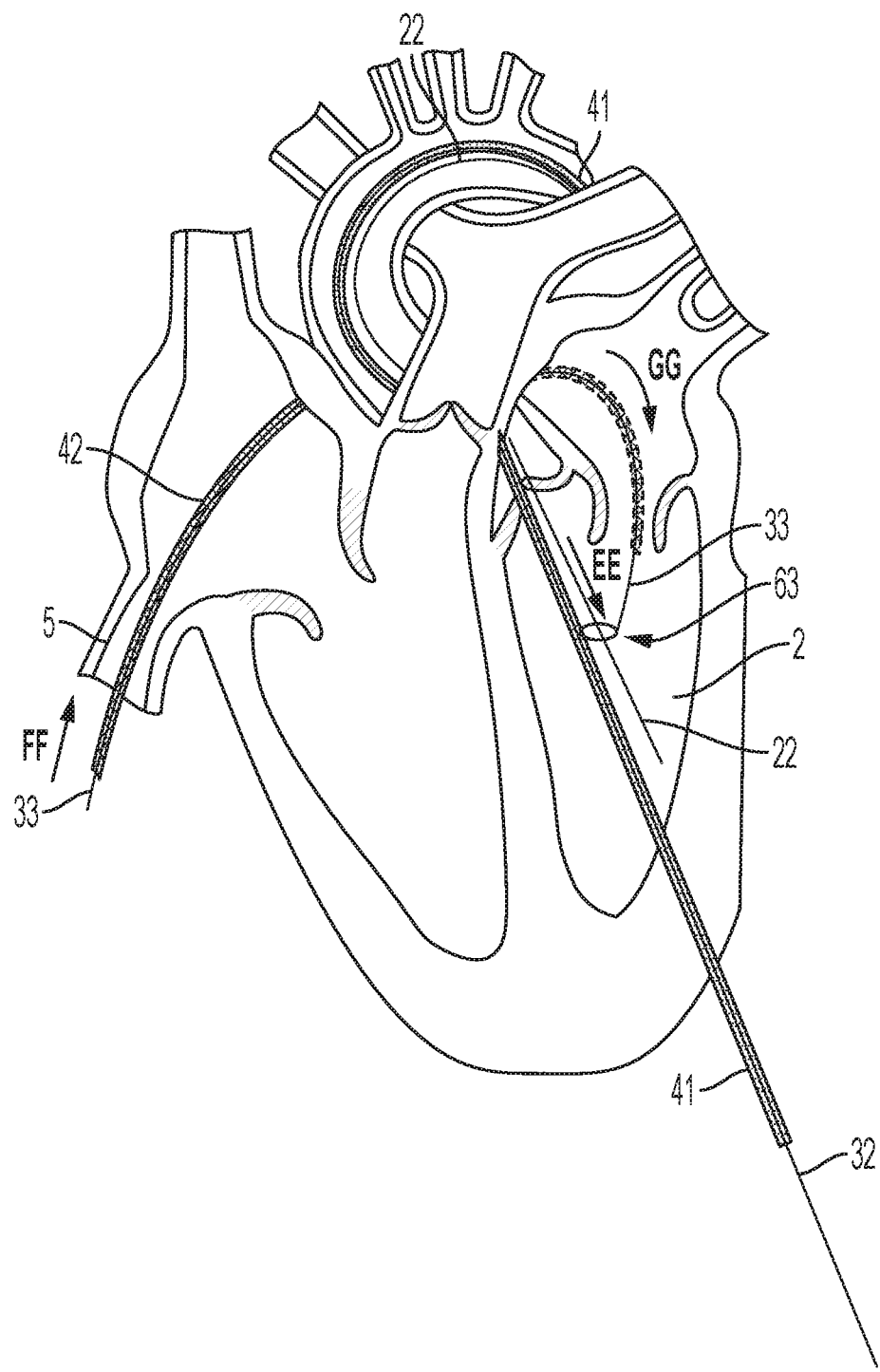
FIG. 11 is a schematic illustration of the heart showing a third snare device routed within the steerable catheter and a loop end of the third snare device snaring the second guidewire within the left ventricle.

Following the positioning of the steerable catheter 42 in the left ventricle 2 of the heart, a third snare device 33 is inserted into a lumen of the steerable catheter 42, at the second access point 13, and routed through the femoral vein 5 in the directions indicated by the arrows FF and GG in FIG. 11, within the steerable catheter 42. The third snare device 33 is then advanced through a distal opening of the lumen of the steerable catheter 42 further into the left ventricle 2 of the heart, and positioned such that a loop end 63 of the third snare device 33 can receive and snare the distal end of the second guidewire 22 that is positioned in the left ventricle 2 as shown in FIG. 11. In some instances, the second guidewire 22 can be advanced in the direction indicated by the arrow EE such that the loop end 63 of the third snare device 33 can ensnare the free end of the second guide wire 22 as it passes further into the left ventricle 2, as shown in FIG. 11.

Figure 12:
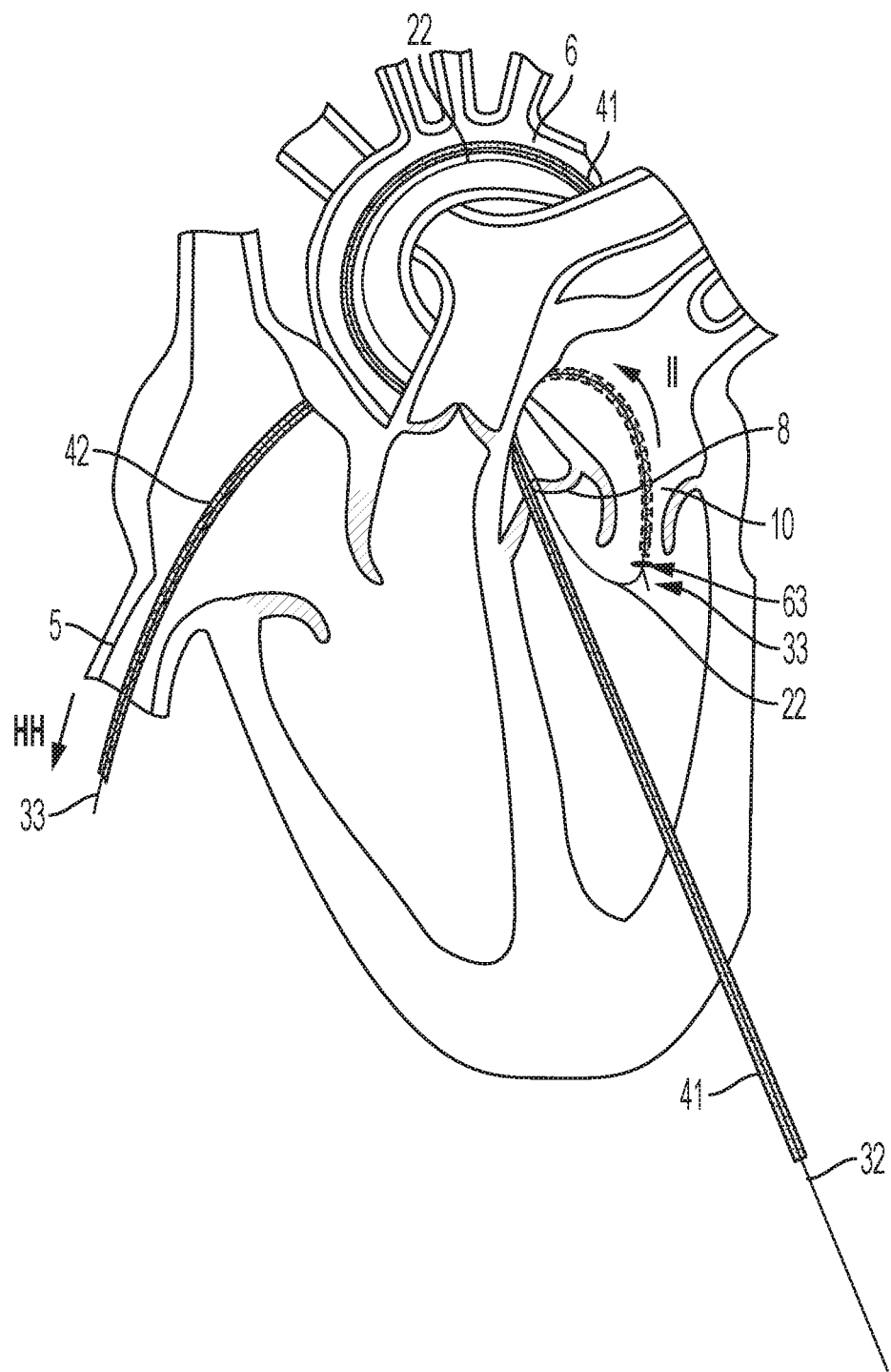
FIG. 12 is a schematic illustration of the heart showing the second guidewire being snared and pulled into the steerable catheter by the third snare device.

As shown in FIG. 12, after the third snare device 33 ensnares the second guidewire 22, the loop end 63 of the third snare device 33 is constricted to tighten the loop end 63 around the second guidewire and allow the third snare device 33 to firmly engage the second guide wire 22.

Figure 13:
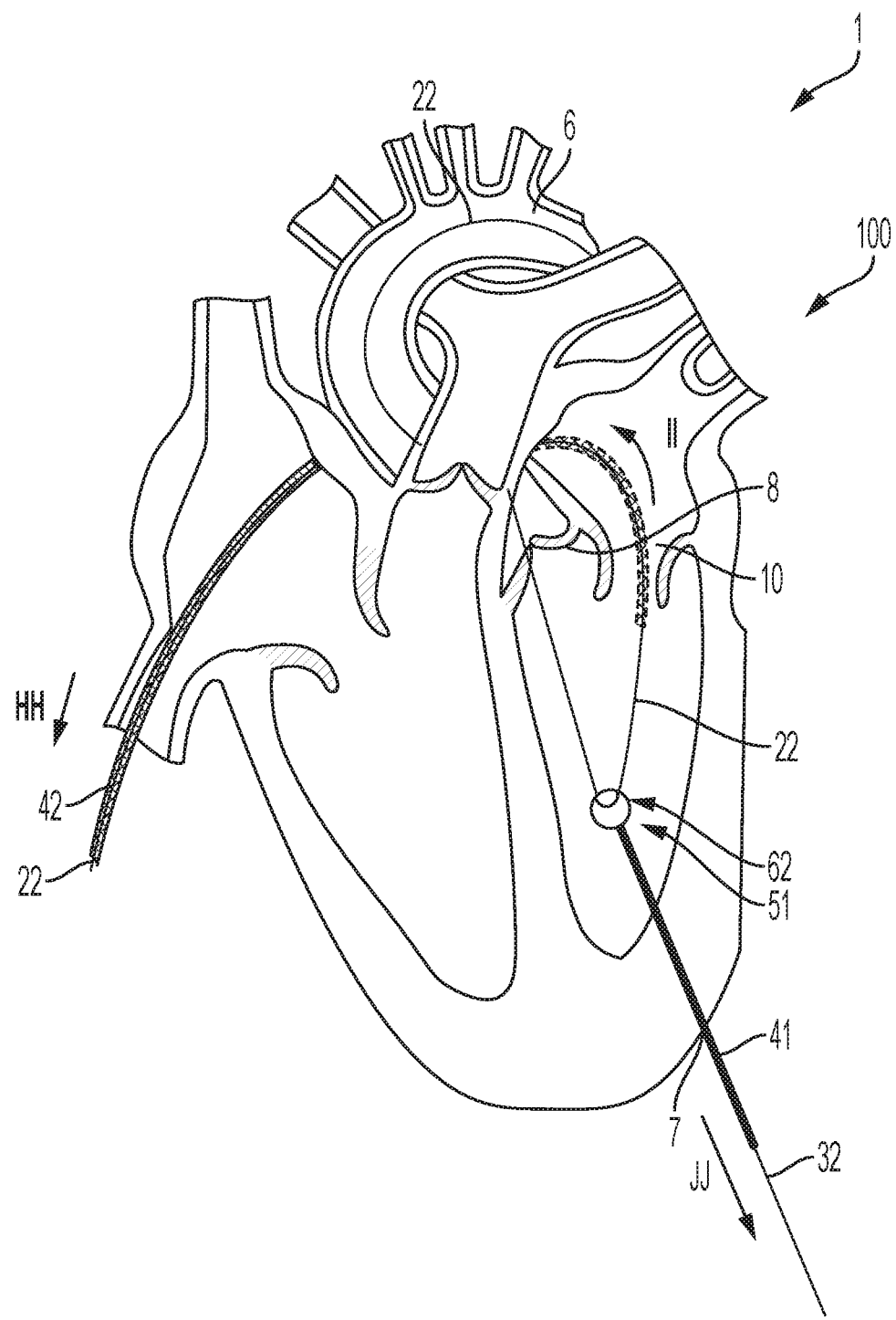
FIG. 13 is a schematic illustration of the heart showing the second guidewire snared and pulled through the steerable catheter, the third snare device removed, the microcatheter pulled proximally though the opening at the apex of the heart, and the second snare device forming, in part, a pulley device in the left ventricle through which the second guidewire is routed from the femoral artery to the femoral vein to form an improved arteriovenous (AV) loop.

FIG. 13 illustrates the establishment of a pulley device to provide an improved AV loop 100. The microcatheter 41, with the second snare device 32 still disposed in its lumen, is withdrawn proximally via the apex 7 of the heart, with the distal wire end of the second snare device 32 also drawn proximally at the apex 7 of the heart drawing the loop end 62 of the second snare device retrograde, through the femoral artery, abdominal aorta, aortic arch 6, aortic valve 8, and into left ventricle 2. This leaves the loop end 62 of the snare device in the position shown in FIG. 13. FIG. 13 also shows the direction of movement of the microcatheter 41 through the apex 7 of the heart 1, in the direction indicated by the arrow JJ. The loop end 62 of the second snare device thus forms a pulley device 51 positioned in the left ventricle 2 of the heart. The pulley device 51 can be positioned to establish the apex of a path for the second guidewire 22 that has concentricity to the aortic valve 8 and the mitral valve 10 of the heart, and prevents the second guidewire 22 from dragging across the native valve apparatus or the tissue between the valves.

Figure 14:
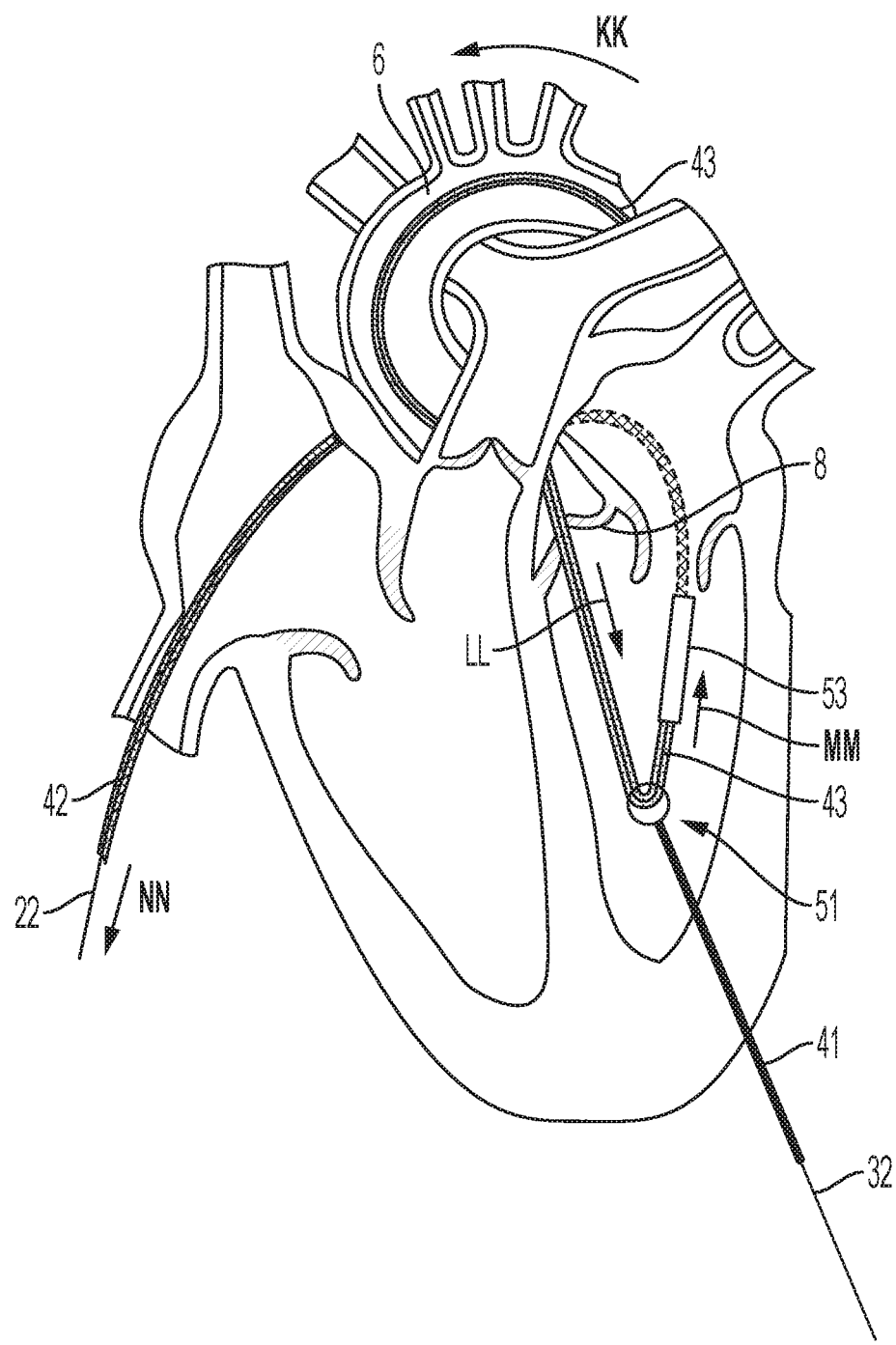
FIG. 14 is a schematic illustration of the heart showing a nosecone balloon catheter disposed over the second guidewire from the femoral artery, through the pulley device, and positioned abutting the distal end of the steerable catheter within the left ventricle.
Figure 15:
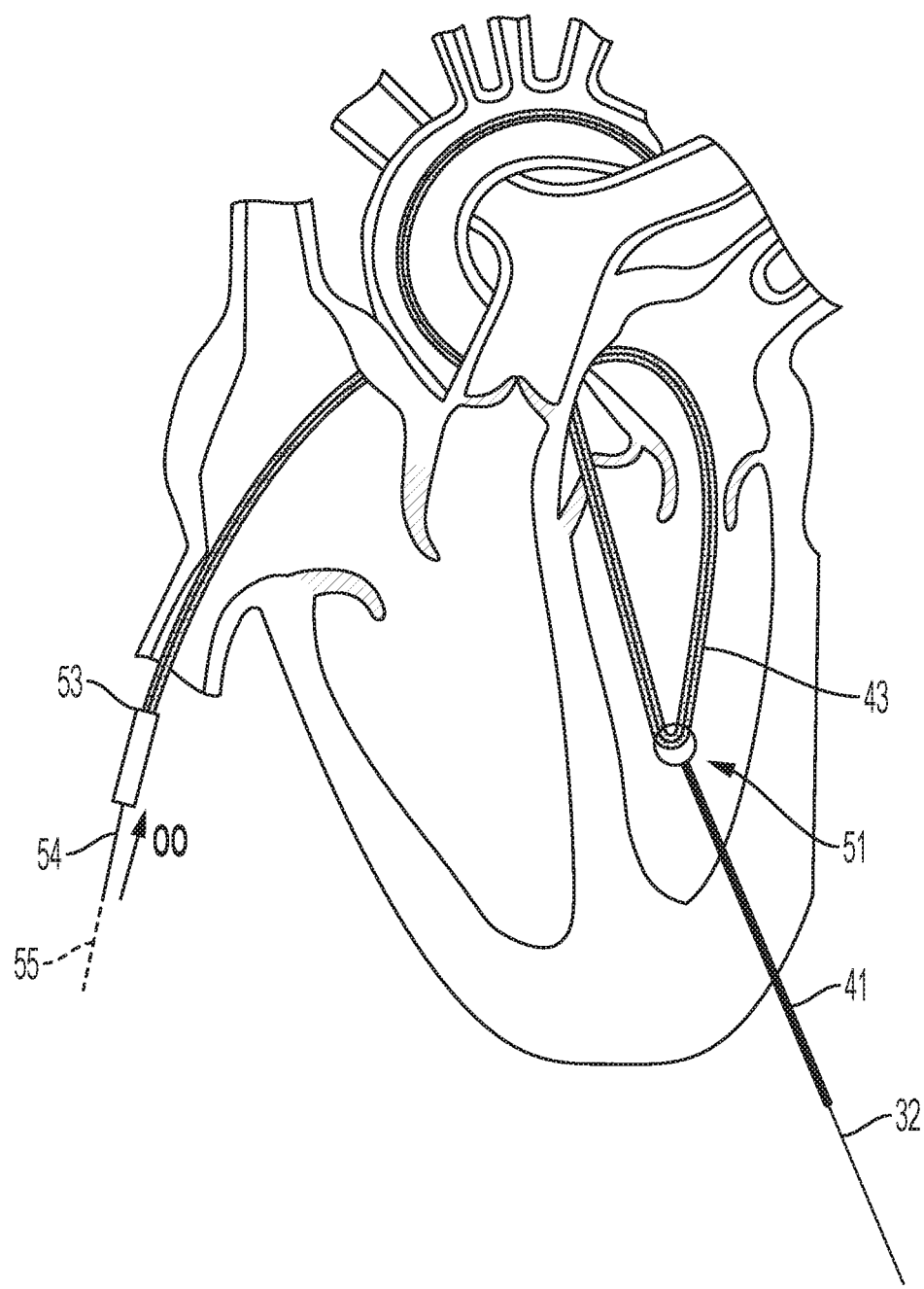
FIG. 15 is a schematic illustration of the heart showing the nosecone balloon catheter after being pulled through the femoral vein access location and the introduction of a valve tether, secured to a prosthetic heart valve, through the lumen of the nosecone balloon catheter at the access location.

FIGS. 14-22 illustrate an exemplary procedure of using the improved AV loop 100 to deploy a prosthetic heart valve. As shown in FIG. 14, a catheter 43, which has a nosecone balloon 53 at its distal end and a lumen therethrough to be deployed over a guidewire is introduced over the second guide wire 22 at the first access point 9 in the femoral artery 12 in the leg of the subject. The catheter 43 (also referred to herein as "nosecone balloon catheter") is advanced in the directions indicated by the arrows KK and LL through the aortic arch 6 and aortic valve 8, through the loop end 62 of the second snare device 32, and positioned with its balloon 53 abutting a distal end of the steerable catheter 42 in the direction of arrow MM.

After positioning the nosecone balloon catheter 43 abutting the steerable catheter 42, the steerable catheter 42 can be pulled proximally, in the direction indicated by the arrow NN, at the second access point 13 and simultaneously, the nosecone balloon catheter 43 can be advanced, such that the catheters 42 and 43 are moved together while maintaining the abutting relationship between the balloon 53 of the nosecone balloon catheter 43 and the distal end of the steerable catheter 42. The catheters 42 and 43 are moved together until the balloon 53 exits the second access point 13 in the femoral vein 5.

In some instances, prior to moving the steerable catheter 42 and the nosecone balloon catheter 43, the nosecone balloon catheter 43 and the steerable catheter 42 can, optionally, each be secured or clamped to the second guide wire 22 at any suitable location along the second guide wire 22, for example, a position outside of the first access point 9 and the second entry location 13 not shown in FIG. 14. A suitable device such as a medical clamp (not shown) can be used to secure the catheters 42 and 43 to the second guidewire 22. This will allow the nosecone balloon catheter 43 and the steerable catheter 42 to each move with the second guide wire 22 and help maintain the abutting relationship between the catheters 42 and 43. In such a case, the length of the second guidewire 22 would need to be sufficiently long to be pulled out through the femoral vein 5 and extend between the femoral vein 5 and the femoral artery 12. The catheters 42 and 43 can be pulled/pushed together with the guidewire 22 until the balloon 53 is disposed outside the second access point 13.

If the catheters 42 and 43 have been clamped to the second guidewire 22 as described above, with the nosecone balloon 53 exteriorized, the catheters 42 and 43 can be detached from the second guide wire 22. The second guidewire 22 can be removed by pulling it outside the access location at the femoral vein 5 or pulling it out the access location at the femoral artery 12. A valve tether 55 that is secured to a prosthetic heart valve 56 (shown in FIGS. 21 and 22) can be inserted into the nosecone balloon catheter 43 in the direction of the arrow OO. More specifically, the valve tether 55 is attached at one end to the prosthetic heart valve 56 and has a wire tether leader 54 disposed at a second end. The tether leader 54 is inserted into a lumen of the nosecone balloon 53 and the tether 55 is routed within the nosecone balloon catheter 43 and exteriorized via the femoral artery 12 at the first access point 9 in the leg of the subject.

Figure 16:
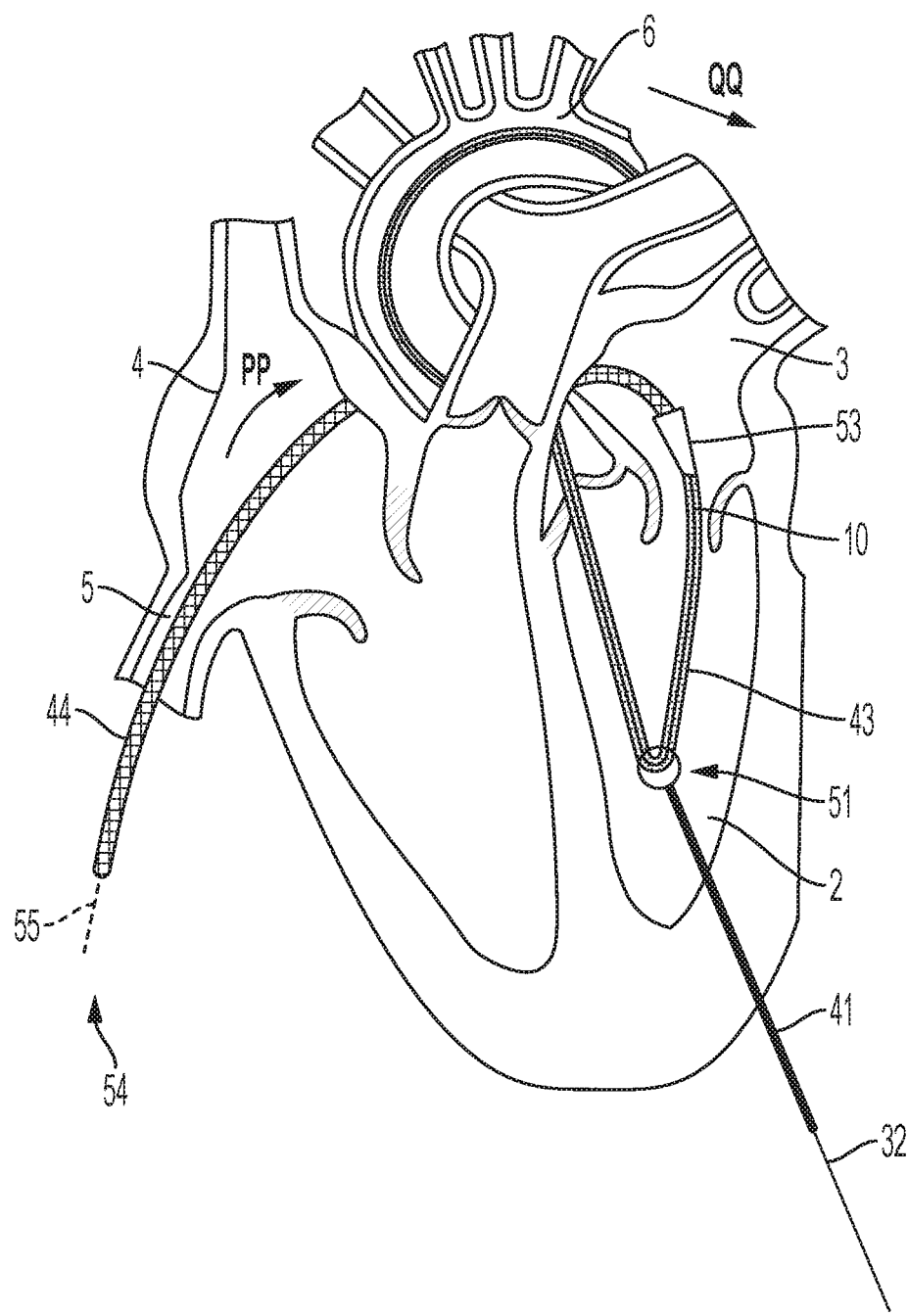
FIG. 16 is a schematic illustration of the heart showing a valve delivery catheter disposed abutting the distal end of the nosecone balloon catheter and advanced into the left atrium of the heart.

Following the routing of the valve tether 55 through the nosecone balloon catheter 43, a valve delivery catheter 44 can then be introduced over the valve tether 55 and disposed abutting the nosecone balloon 53 of the nosecone balloon catheter 43. As shown in FIG. 16, the valve delivery catheter 44 can be moved in the direction of arrows PP, pushing the nosecone balloon catheter 43 therewith, through the femoral vein 5 and into the right atrium 4. The nosecone balloon 53 is then inflated to provide a lead-in for the valve delivery catheter 44 and the nosecone balloon catheter 43 and catheter 44 are then moved through the transseptal puncture into the left atrium 3 to position a distal end of the catheter 44 within the left atrium 3, as illustrated in FIG. 16.

Figure 17:
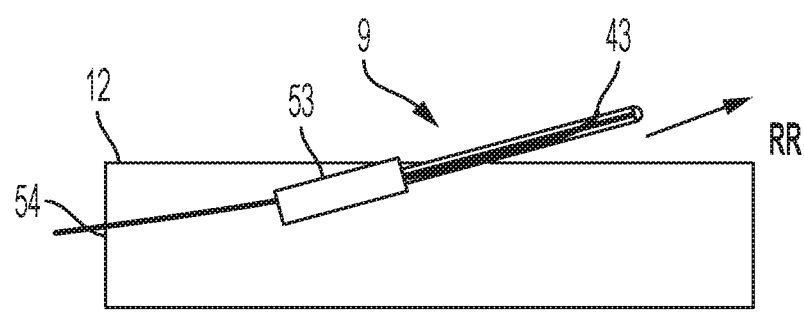
FIG. 17 is a schematic illustration of the femoral artery in a leg showing the removal of the nosecone balloon leaving the valve tether in place.
Figure 18:
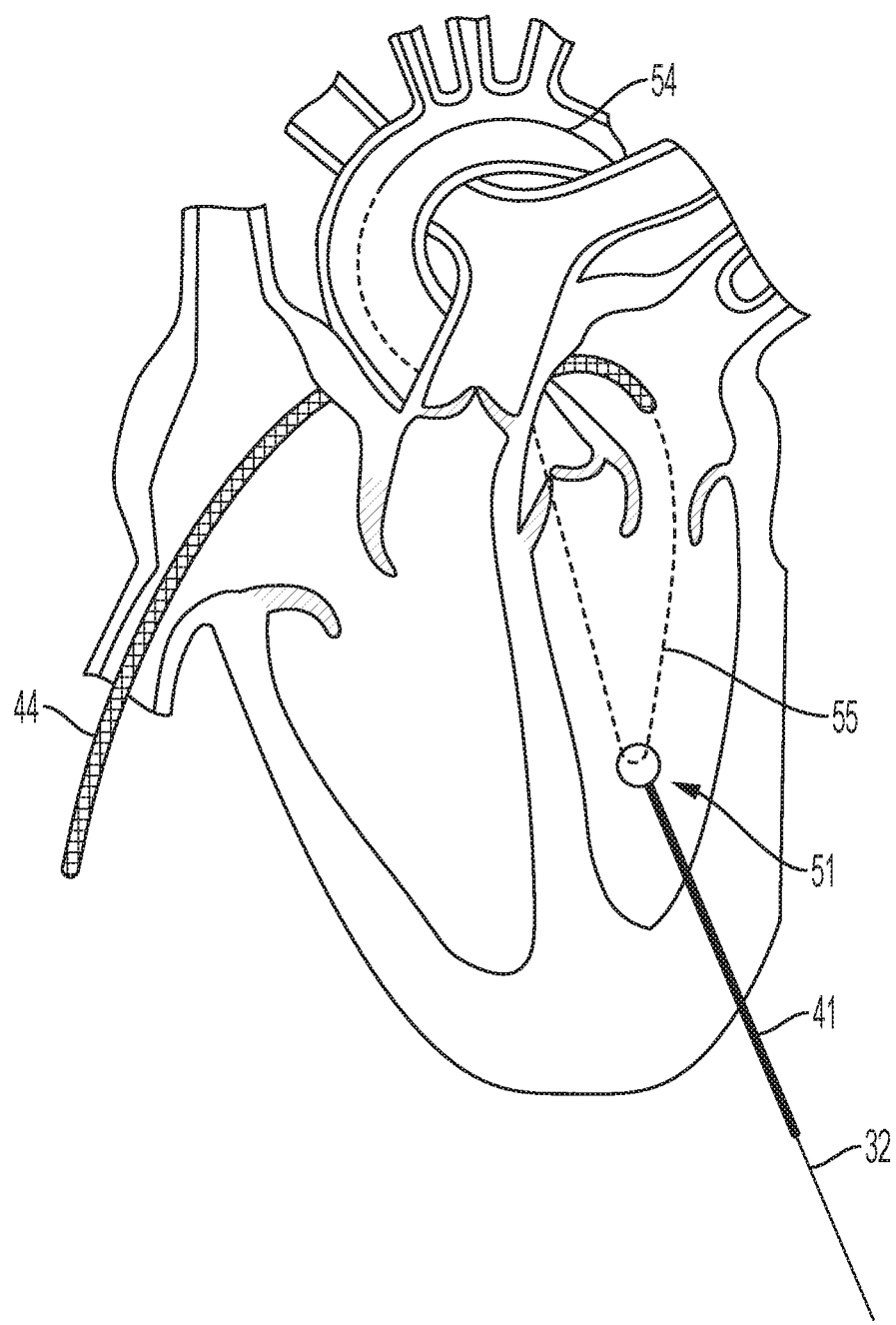
FIG. 18 is a schematic illustration of the heart showing the valve tether extending through the AV loop after the nosecone balloon catheter has been removed through the femoral artery access location, with the valve delivery catheter disposed over a portion of the valve tether.

Following the positioning of the valve delivery catheter 44 in the left atrium 3, the balloon 53 of the nosecone balloon catheter 43 is deflated and the catheter 43 is removed via the aortic arch 6, in the direction of the arrow QQ in FIG. 16, and via the first access point 9 in the leg of the subject, as shown in FIG. 17. At the first access point 9, the nosecone balloon catheter 43 is removed (indicated by arrow RR) from the femoral artery 12 leaving in place the valve tether 55 with the valve tether leader 54 visible at the femoral artery end, as indicated in FIGS. 17 and 18. Notably, the nosecone balloon catheter does not pass through the apex 7 of the heart. Instead, the nosecone balloon catheter is inserted through the femoral vein 5 of the patient and is exteriorized at the first access point 9 in the femoral artery 12 of the patient. As a result, the incision made in the apex 7 of the heart may be 3-4 Fr (as opposed to 8 Fr or greater as would otherwise be required to accommodate the nosecone balloon catheter). This technique thus allows for increased freedom in the design of the nosecone balloon catheter. For example, the nosecone balloon catheter may have an increased diameter and a more robust design as the nosecone balloon catheter need not have a diameter small enough to pass through the apex 7 of the heart interventionally.

Figure 19:
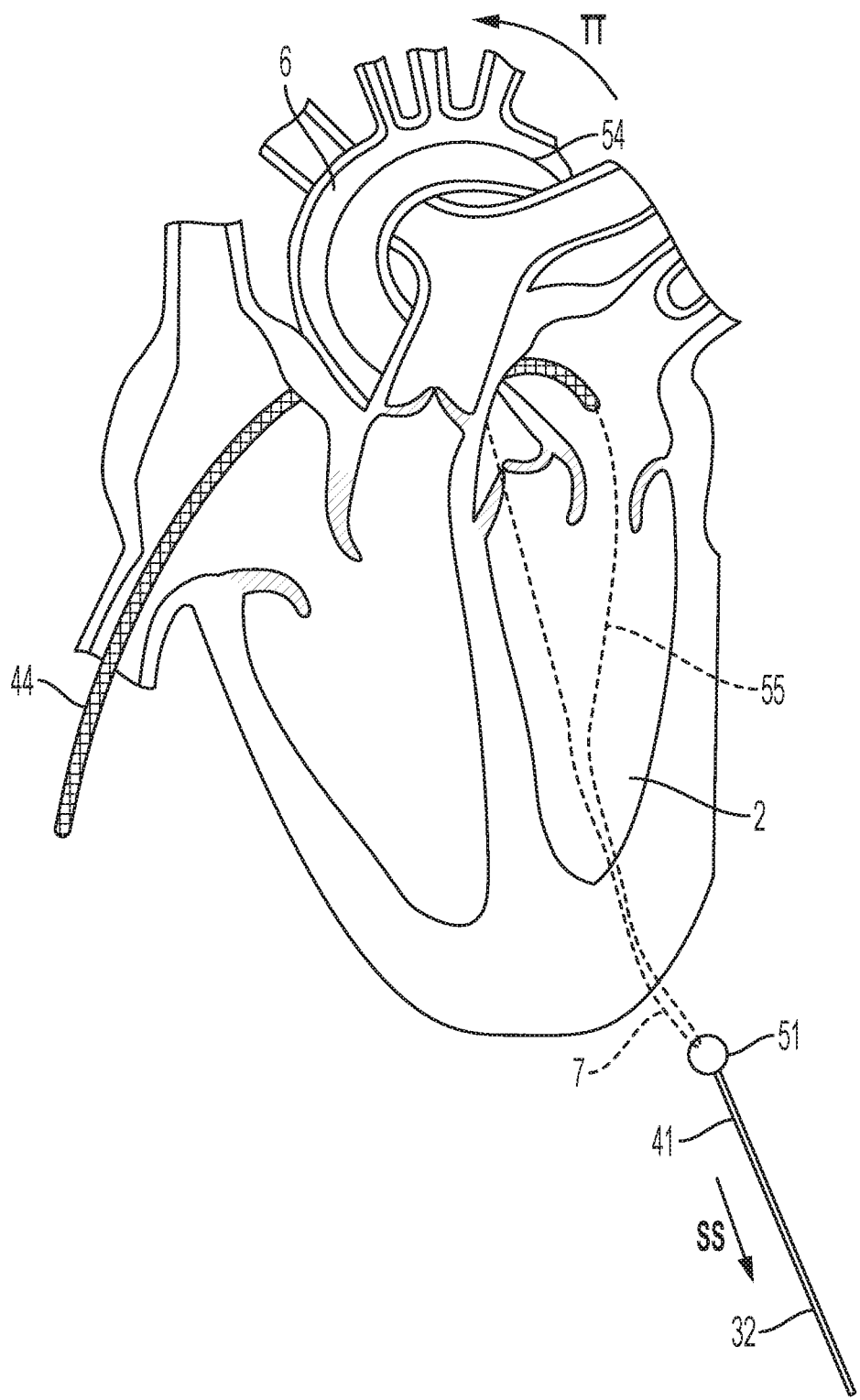
FIG. 19 is a schematic illustration of the heart showing the exteriorization of the valve tether doubled backed through the apex of the heart after the pulley device is pulled through the apex.
Figure 20:
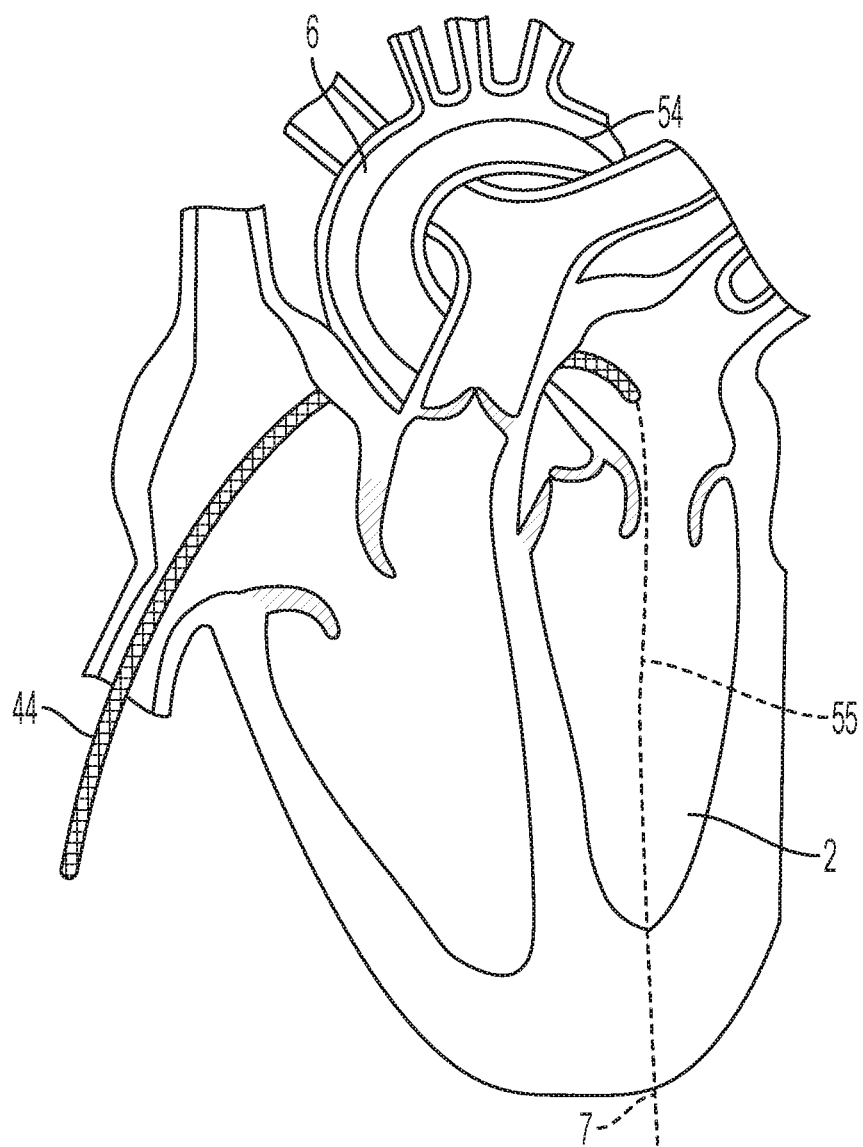
FIG. 20 is a schematic illustration of the heart showing the valve tether extending from the femoral vein via the delivery catheter to the apex of the heart after the leader end of the tether is pulled proximally by the second snare device from the femoral artery and through the apex.

As shown in FIG. 19, the microcatheter 41 including the second snare device 32 forming the pulley device 51 are retracted out of the left ventricle 2 of the heart by pulling them proximally through the opening in the apex 7, in the direction indicated by the arrow SS. This retraction of the second snare device 32 pulls the valve tether 55 through the apex 7 of the heart, in a doubled back configuration as shown in FIG. 19, with the portion of the valve tether 55 or the valve tether leader 54 in the femoral artery 12 being retracted in the direction of the arrow TT. With further retraction and removal of the microcatheter 41 and the second snare device 32, the portions of the valve tether 55 in the femoral artery 12 are fully retracted and exteriorized via the apex 7, as shown in FIG. 20.

Figure 21:
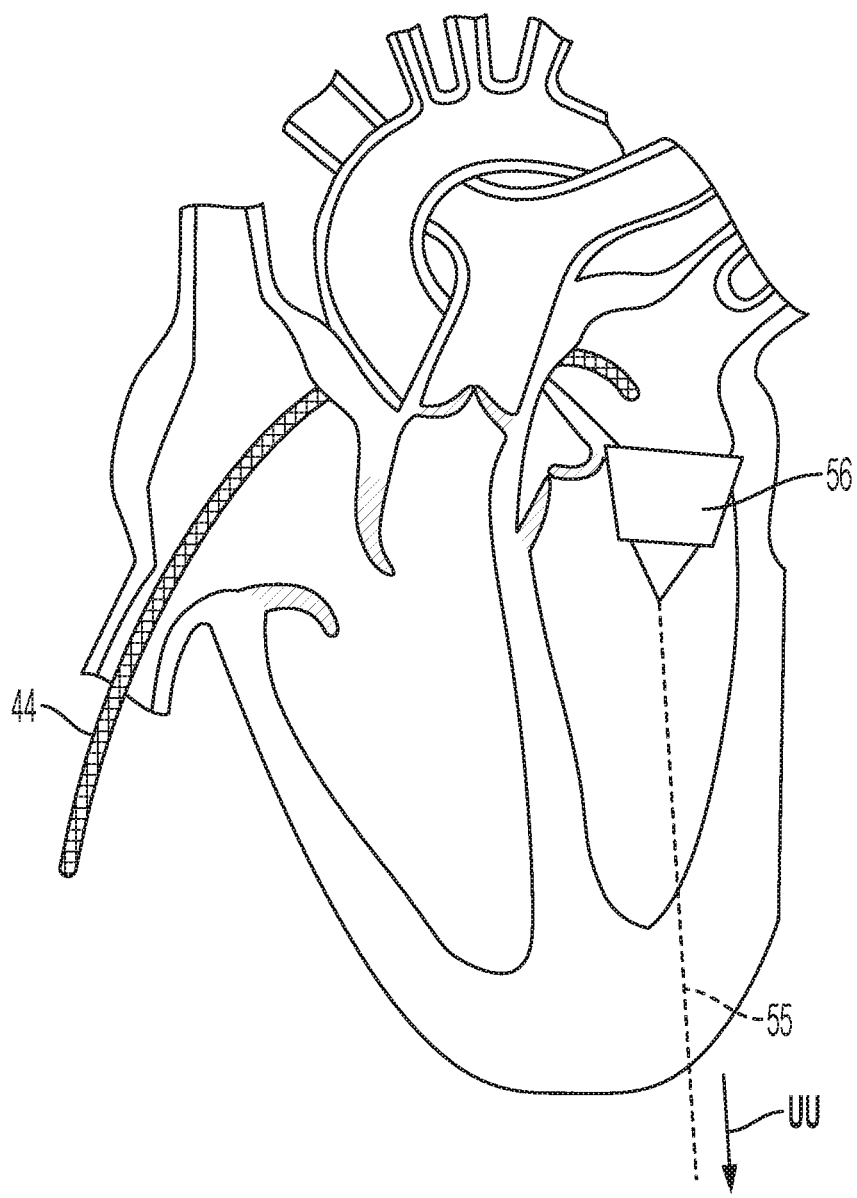
FIG. 21 is a schematic illustration of the heart showing the deployment of a prosthetic valve attached to the valve tether.
Figure 22:
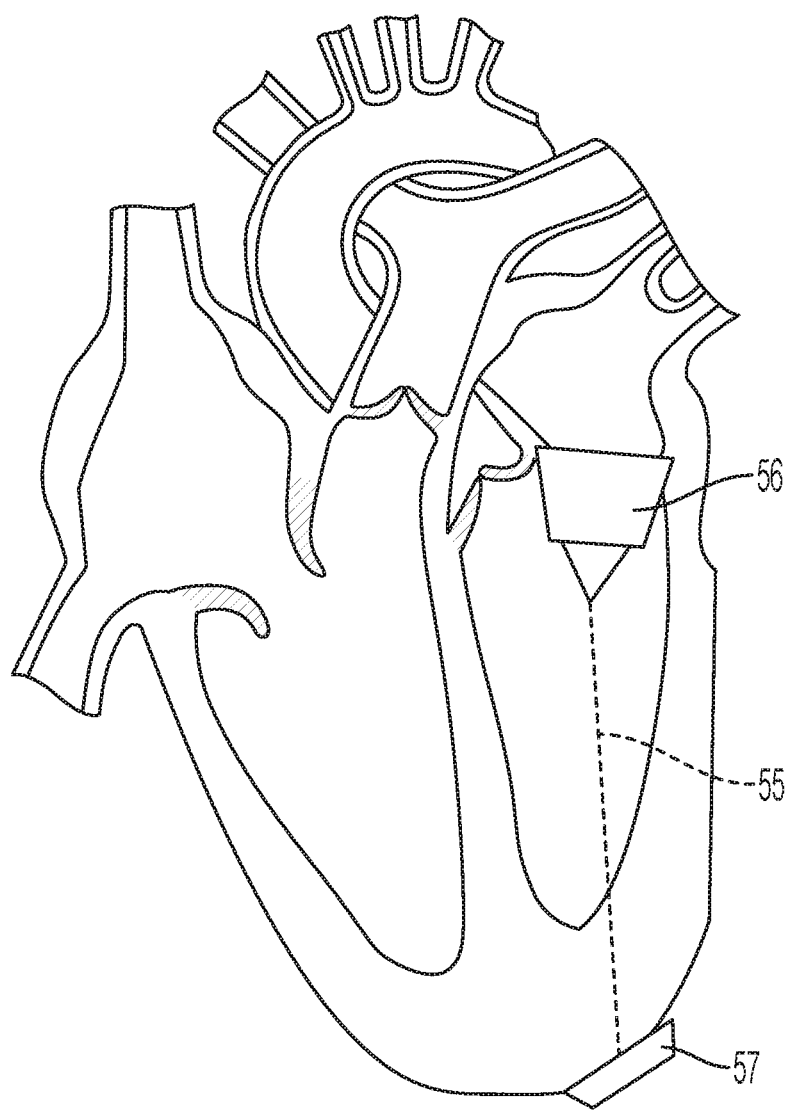
FIG. 22 is a schematic illustration of the heart showing the deployment of an epicardial pad to anchor the prosthetic valve attached to the valve tether.

The valve delivery catheter 44 is then used to deliver the prosthetic heart valve 56 by pulling the valve tether 55 extending through the apex 7 proximally in the direction indicated by the arrow UU in FIG. 21 and/or by pushing the prosthetic valve 56 out of the distal end of the delivery catheter 44. Following the deployment and positioning of the prosthetic heart valve 56, the apical entry site can be used to attach an epicardial pad 57, as shown in FIG. 22, or any other suitable anchoring device to anchor the prosthetic heart valve 56 in place via the valve tether 55.

Figure 23A:
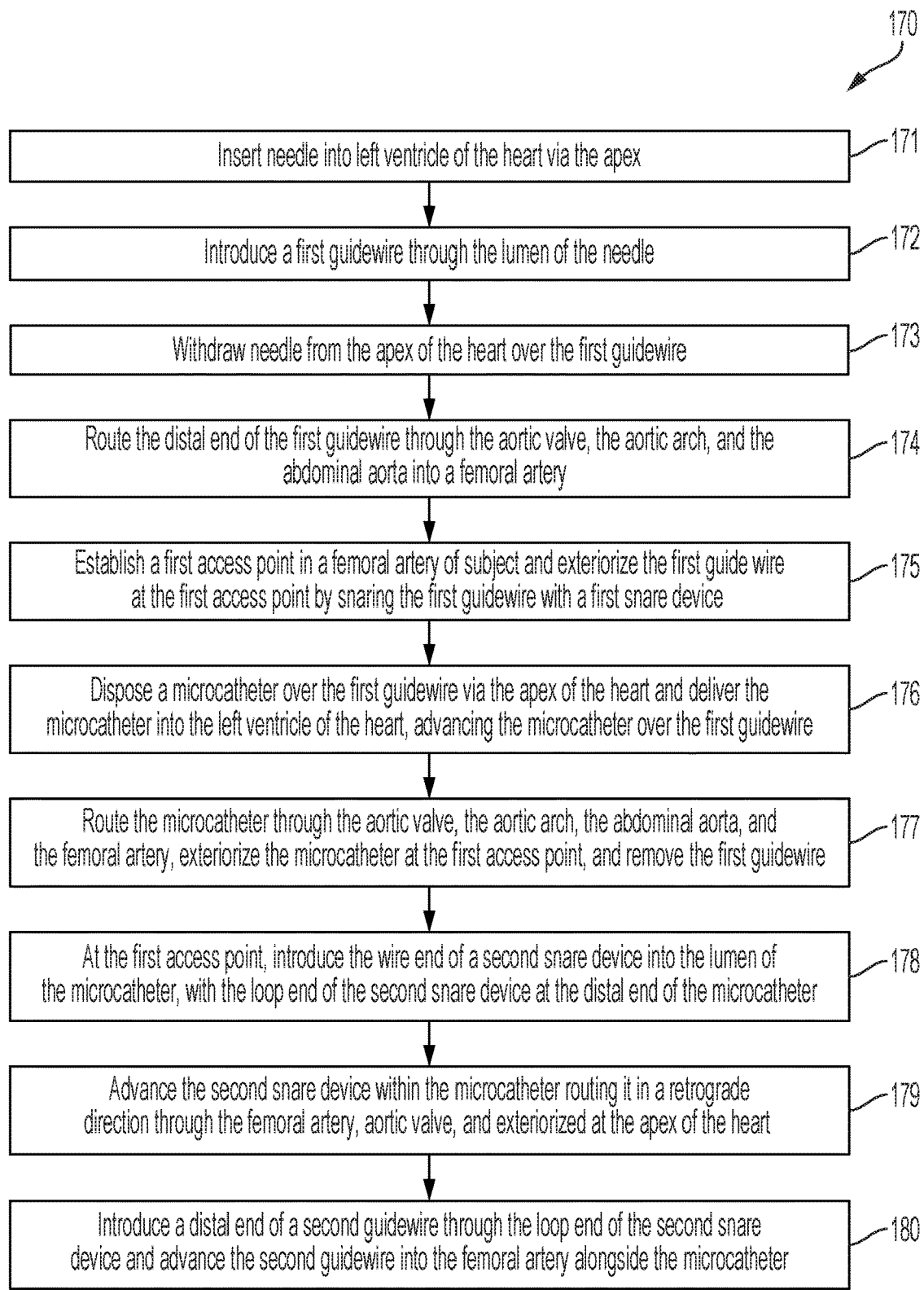
FIGS. 23A and 23B show a flow chart illustrating a method of establishing an AV loop, according to an embodiment.
Figure 23B:
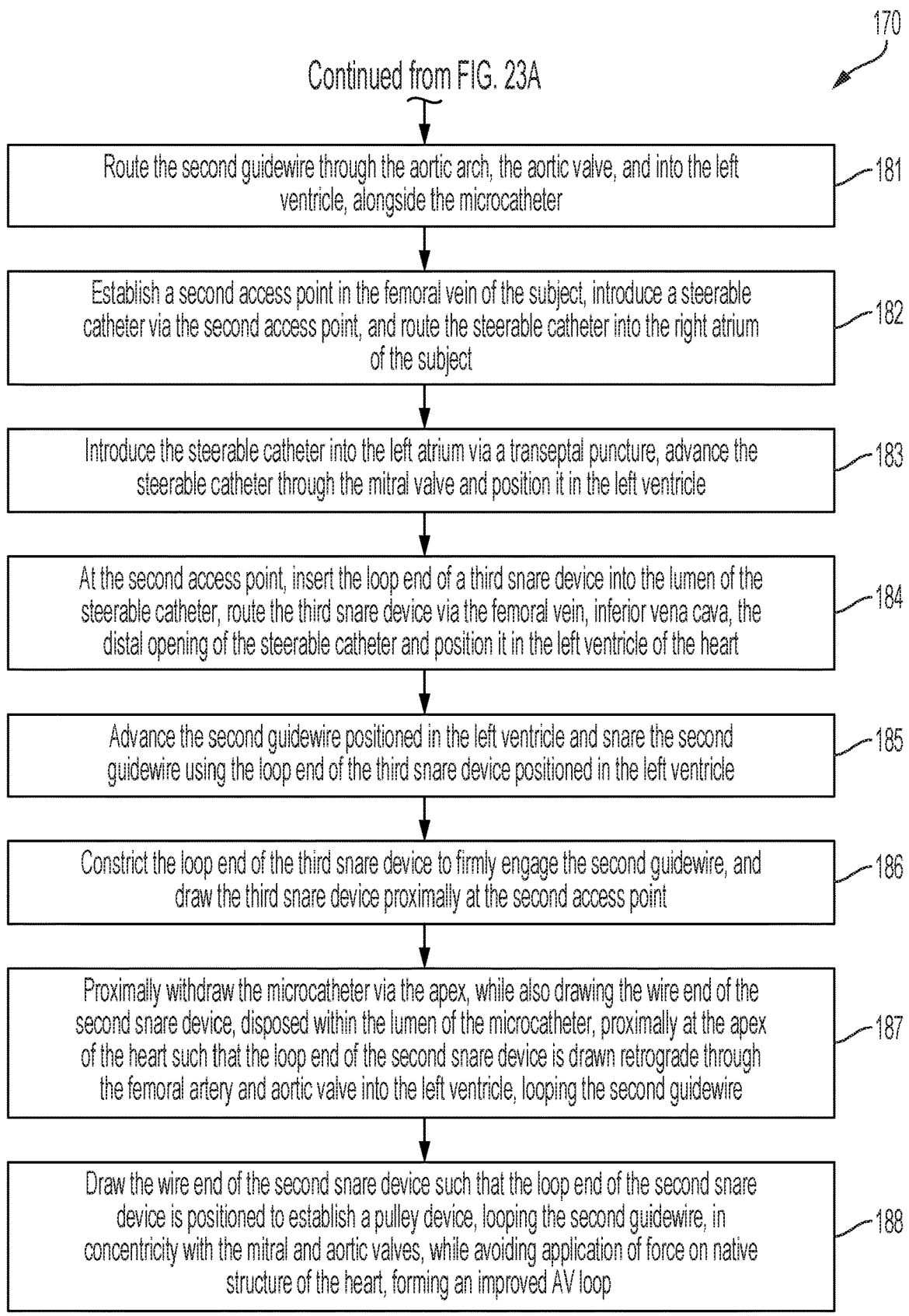

FIGS. 23A and 23B illustrate an example method 150 of establishing an AV loop as described herein. In the method 170, a needle is inserted into the left ventricle of the heart of a subject via the apex of the heart and a first guidewire is introduced through the lumen of the needle, followed by withdrawal of the needle, at 171, 172, and 173. The first guidewire is routed through the aortic valve, the aortic arch, and the abdominal aorta into a femoral artery and is exteriorized, using a first snare device, at a first access point established in the femoral artery in a leg of the subject, at 174 and 175.

A microcatheter is then disposed over the first guidewire and advance via the apex and routed through the antegrade path and exteriorized at the first access point in the femoral artery, removing the first guidewire, at 176 and 177. Following the removal of the first guidewire, at the first access point, the wire end of a second snare device is introduced into the lumen of the microcatheter and routed retrograde through the femoral artery, aortic arch, aortic valve and then exteriorized at the apex, at 178 and 179.

A distal end of a second guidewire is then introduce through the loop end of the second snare device and then advanced outside but alongside the microcatheter, retrograde through the femoral artery, aortic arch and aortic valve to be positioned within the left ventricle of the heart, at 180 and 181.

A second access point is establish in a femoral vein of the subject and a steerable catheter is introduced through the second access point and routed through the inferior vena cava into the right atrium of the heart at 182. Following which it is advanced, through a transeptal puncture, into the left atrium of the heart, and through the mitral valve to be positioned in the left ventricle, at 183.

The loop end of a third snare device is inserted into the lumen of the steerable catheter at the second access point, and the third snare device is advanced retrograde through the distal opening of the steerable catheter, into the left ventricle, at 184. The second guide wire is then advance while positioning the third snare device such that the third snare device can snare the free end of the second guidewire within the left ventricle, at 185. After snaring the second guidewire the loop end of the third snare device is constricted to firmly engage the second guidewire and the third snare device is drawn proximally at the second access point to have the second guidewire drawn through the steerable catheter and exteriorized at the second access point, at 186.

The microcatheter is then withdrawn proximally at the apex while also drawing proximally, the second snare device disposed within the microcatheter, with the loop end of the second snare device being drawn retrograde through the femoral artery, the aortic arch, and the aortic valve into the left ventricle, looping the second guidewire, at 187. The proximal wire end of the second snare device can then be suitably drawn proximally to position the loop end of the second snare device within the left ventricle such that the loop end forms a pulley device looping the second guidewire, establishing an improved AV loop, at 188. The loop end of the second snare device can be positioned such that the loop end forms a pulley device that is concentric with the aortic and mitral valves, while avoiding direct application of force on the aortic and/or mitral valves or other anatomical structures.

While the example procedure of valve deployment described the use of the improved AV loop 100 to deploy a prosthetic mitral valve, the improved AV loop can be used for any number of interventions including deployment, positioning, or other suitable treatment of any number of native or prosthetic structures (e.g. aortic valve, tricuspid valve, pulmonary valve, or other cardiac or vascular structures). In other words, although some embodiments are described herein with reference to a prosthetic mitral valve, it should be understood that the apparatus and methods described herein can be used to deliver any other type of heart valve. For example, with the same AV loop described above, a prosthetic aortic valve can be delivered into the native aortic valve 8, either retrograde from the first access point, or transseptally from the second access point. Furthermore, it will be understood that while retrograde delivery has been described herein as accessed through the femoral vein of the patient, such access is merely exemplary, and may be substituted, for example, with jugular access.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

To summarize the foregoing, a method of establishing an arteriovenous loop in a heart of a patient for delivery of a transcatheter prosthetic valve, includes inserting a first catheter into a first access point of the patient, the catheter having a leading end, a trailing end opposite the leading end and a lumen extending between the leading and trailing ends, positioning the leading end of the first catheter in the left ventricle of the heart, inserting a first snare device into the lumen of the first catheter, the first snare device having a loop at a leading end of the first snare device, advancing the leading end of the first snare device through the leading end of the first catheter such that the loop of the first snare device is positioned in the left ventricle of the heart, inserting a first guidewire into a second access point of the patient different than the first access point, the first guidewire having a leading end, positioning the first guidewire into the left ventricle of the patient and ensnaring the guidewire in the loop of the first snare device to form an arteriovenous loop such that a first portion of the arteriovenous loop traversing the native aortic valve and a second portion of the arteriovenous loop traversing the native mitral valve are spaced from the native aortic valve annulus and the native mitral valve annulus; and/or the first access point may be the femoral vein, and the step of positioning the first catheter may further include routing the leading end of the first catheter from the femoral vein into the left atrium of the heart via a transseptal puncture, through the mitral valve, and into the left ventricle of the heart, and the second access point may be the femoral artery, and the step of positioning the first guidewire may include routing the leading end of the first guidewire from the femoral artery through the aortic arch, the aortic valve and into the left ventricle of the heart; and/or the left ventricle of the heart may be punctured; and/or a leading end of a second guidewire may extend through the puncture and into the left ventricle of the heart; and/or the puncture may be created using a needle having a lumen and the leading end of the second guidewire may be inserted into the left ventricle of the heart through the lumen of the needle; and/or the needle may extend over the second guidewire after the leading end of the second guidewire has been inserted into the left ventricle of the heart; and/or the leading end of the second guidewire may be advanced from the left ventricle of the heart, through the aortic valve, the aortic arch, the abdominal aorta, into a femoral artery and the leading end of the second guidewire may be exteriorized through the second access point; and/or a second catheter may be advanced over the second guidewire, the second catheter having a leading end, a trailing end opposite the leading end and a lumen extending between the leading and trailing ends; and/or a second snare device may be inserted into the lumen of the second catheter, the second snare device having a leading end and a loop opposite the leading end, and the leading end of the second snare device may be advanced through the second catheter to exteriorize the leading end of the second snare device from the left ventricle of the heart, wherein the loop of the second snare device is positioned adjacent the access point and outside the lumen of the second catheter; and/or the first guidewire may be routed through the loop of the second snare device, along an exterior sidewall of the second catheter and into the left ventricle of the heart; and/or the second catheter may be retracted, the loop of the second snare may be retracted over the first guidewire and into the left ventricle of the patient; and/or the second snare device may be pulled to apply tension to the arteriovenous loop during delivery of a prosthetic valve to ensure that the first and second portions of the arteriovenous loop remain spaced from the native aortic valve annulus and the native mitral valve annulus; and/or a prosthetic heart valve may be delivered over the atrioventricular loop; and/or the prosthetic heart valve may be delivered to and implanted within the native mitral valve annulus; and/or a third catheter may be inserted into the second access point of the patient and over the first guidewire, the third catheter having a leading end with a nosecone balloon and a trailing end opposite the leading end, and the nosecone balloon may be advanced from the second access point, through the loop of the second snare device and into abutment with the leading end of the first catheter; and/or each of the first catheter and the third catheter may be clamped to the first guidewire; and/or the nosecone balloon may be exteriorized through the first access point; and/or a tether of the prosthetic heart valve may be inserted into the third catheter, the prosthetic heart valve including a collapsible and expandable stent and a plurality and plurality of leaflets disposed within the stent, a leading end of a valve delivery catheter may be placed into abutment with the nosecone balloon, the valve delivery catheter and the nosecone balloon catheter may be advanced into the right atrium of the heart, the nosecone balloon may be inflated, the nosecone balloon and the valve delivery catheter may be advanced through the transseptal puncture and into the left atrium, and the nosecone balloon may then be deflated and removed from the second access point of the patient; and/or the prosthetic heart valve may be deployed from the valve delivery catheter, the tether of the prosthetic heart valve may be pulled through the puncture in the left ventricle and an anchoring device may be attached to the apex of the heart to anchor the prosthetic heart; and/or the loop of the second snare device may be retracted through the puncture in the left ventricle to exteriorize the tether before the prosthetic heart valve may be deployed from the valve delivery catheter.

The invention claimed is:
1. A method of establishing an arteriovenous loop in a heart of a patient for delivery of a transcatheter prosthetic valve, the method comprising:
  inserting a first catheter into a first access point of the patient, the catheter having a leading end, a trailing end opposite the leading end and a lumen extending between the leading and trailing ends;

positioning the leading end of the first catheter in the left ventricle of the heart;

inserting a first snare device into the lumen of the first catheter, the first snare device having a loop at a leading end of the first snare device;

advancing the leading end of the first snare device through the leading end of the first catheter such that the loop of the first snare device is positioned in the left ventricle of the heart;

inserting a first guidewire into a second access point of the patient different than the first access point, the first guidewire having a leading end;

positioning the first guidewire into the left ventricle of the patient; and ensnaring the guidewire in the loop of the first snare device to form an arteriovenous loop such that a first portion of the arteriovenous loop traversing the native aortic valve and a second portion of the arteriovenous loop traversing the native mitral valve are spaced from the native aortic valve annulus and the native mitral valve annulus.

2. The method of claim 1, wherein the first access point is the femoral vein, and the step of positioning the first catheter comprises routing the leading end of the first catheter from the femoral vein into the left atrium of the heart via a transseptal puncture, through the mitral valve, and into the left ventricle of the heart, and wherein the second access point is the femoral artery, and the step of positioning the first guidewire comprises routing the leading end of the first guidewire from the femoral artery through the aortic arch, the aortic valve and into the left ventricle of the heart.

3. The method of claim 1, further comprising puncturing the left ventricle of the heart.

4. The method of claim 3, further comprising:
inserting a leading end of a second guidewire through the puncture and into the left ventricle of the heart.

5. The method of claim 4, wherein the puncture is created using a needle having a lumen and the leading end of the second guidewire is inserted into the left ventricle of the heart through the lumen of the needle.

6. The method of claim 5, further comprising withdrawing the needle over the second guidewire after the leading end of the second guidewire has been inserted into the left ventricle of the heart.

7. The method of claim 4, further comprising advancing the leading end of the second guidewire from the left ventricle of the heart, through the aortic valve, the aortic arch, the abdominal aorta, into a femoral artery and exteriorizing the leading end of the second guidewire through the second access point.

8. The method of claim 7, further comprising:
advancing a second catheter over the second guidewire, the second catheter having a leading end, a trailing end opposite the leading end and a lumen extending between the leading and trailing ends.

9. The method of claim 8, further comprising:
inserting a second snare device into the lumen of the second catheter, the second snare device having a leading end and a loop opposite the leading end; and
advancing the leading end of the second snare device through the second catheter to exteriorize the leading end of the second snare device from the left ventricle of the heart, wherein the loop of the second snare device is positioned adjacent the access point and outside the lumen of the second catheter.

10. The method of claim 9, wherein the first guidewire is routed through the loop of the second snare device, along an exterior sidewall of the second catheter and into the left ventricle of the heart.

11. The method of claim 10, further comprising:
retracting the second catheter; and
retracting the loop of the second snare device over the first guidewire and into the left ventricle of the patient.

12. The method of claim 11, further comprising:
pulling the second snare device to apply tension to the arteriovenous loop during delivery of a prosthetic valve to ensure that the first and second portions of the arteriovenous loop remain spaced from the native aortic valve annulus and the native mitral valve annulus.

13. The method of claim 12, further comprising delivering a prosthetic heart valve over the atrioventricular loop.

14. The method of claim 13, wherein the prosthetic heart valve is delivered to and implanted within the native mitral valve annulus.

15. The method of claim 11, further comprising:
inserting a third catheter into the second access point of the patient and over the first guidewire, the third catheter having a leading end with a nosecone balloon and a trailing end opposite the leading end; and
advancing the nosecone balloon from the second access point, through the loop of the second snare device and into abutment with the leading end of the first catheter.

16. The method of claim 15, further comprising:
clamping each of the first catheter and the third catheter to the first guidewire.

17. The method of claim 15, further comprising:
exteriorizing the nosecone balloon through the first access point.

18. The method of claim 15, further comprising:
inserting a tether of the prosthetic heart valve into the third catheter, the prosthetic heart valve comprising a collapsible and expandable stent and a plurality and plurality of leaflets disposed within the stent;
placing a leading end of a valve delivery catheter into abutment with the nosecone balloon;
advancing the valve delivery catheter and the nosecone balloon catheter into the right atrium of the heart;
inflating the nosecone balloon;
advancing the nosecone balloon and the valve delivery catheter through the transseptal puncture and into the left atrium; and
deflating the nosecone balloon and removing the nosecone balloon from the second access point of the patient.

19. The method of claim 18, further comprising:
deploying the prosthetic heart valve from the valve delivery catheter;
pulling the tether of the prosthetic heart valve through the puncture in the left ventricle; and
attaching an anchoring device to the apex of the heart to anchor the prosthetic heart.

20. The method of claim 19, further comprising retracting the loop of the second snare device through the puncture in the left ventricle to exteriorize the tether before deploying the prosthetic heart valve from the valve delivery catheter.

* * * * *